United States Patent
Blaha

(10) Patent No.: US 11,090,165 B2
(45) Date of Patent: Aug. 17, 2021

(54) KNEE PROSTHETIC IMPLANT

(71) Applicant: EVA15 LLC, Ann Arbor, MI (US)

(72) Inventor: J. David Blaha, Ann Arbor, MI (US)

(73) Assignee: EVA15 LLC, Ann Arbor, MI (US)

( * ) Notice: Subject to any disclaimer, the term of this patent is extended or adjusted under 35 U.S.C. 154(b) by 192 days.

(21) Appl. No.: 16/066,783

(22) PCT Filed: Dec. 29, 2016

(86) PCT No.: PCT/US2016/069088
§ 371 (c)(1),
(2) Date: Jun. 28, 2018

(87) PCT Pub. No.: WO2017/117337
PCT Pub. Date: Jul. 6, 2017

(65) Prior Publication Data
US 2019/0000633 A1    Jan. 3, 2019

Related U.S. Application Data

(60) Provisional application No. 62/272,962, filed on Dec. 30, 2015.

(51) Int. Cl.
*A61F 2/38* (2006.01)
*A61F 2/30* (2006.01)

(52) U.S. Cl.
CPC ............ *A61F 2/3886* (2013.01); *A61F 2/389* (2013.01); *A61F 2/3859* (2013.01); *A61F 2002/30934* (2013.01)

(58) Field of Classification Search
CPC .................................................. A61F 2/3886
See application file for complete search history.

(56) References Cited

U.S. PATENT DOCUMENTS

| | | | |
|---|---|---|---|
| 4,224,697 A | 9/1980 | Murray et al. | |
| 4,959,071 A * | 9/1990 | Brown | A61F 2/3886 623/20.27 |
| 5,007,933 A * | 4/1991 | Sidebotham | A61F 2/3886 623/20.27 |
| 5,011,496 A * | 4/1991 | Forte | A61F 2/385 623/20.18 |
| 5,116,375 A * | 5/1992 | Hofmann | A61F 2/3886 623/20.27 |
| 5,387,240 A | 2/1995 | Pottenger et al. | |
| 5,658,342 A | 8/1997 | Draganich et al. | |
| 6,019,794 A | 2/2000 | Walker | |
| 6,540,787 B2 | 4/2003 | Biegun et al. | |

(Continued)

OTHER PUBLICATIONS

International Search Report dated Mar. 13, 2017.
(Continued)

*Primary Examiner* — Bruce E Snow
*Assistant Examiner* — Melissa A Hoban
(74) *Attorney, Agent, or Firm* — Dickinson Wright PLLC

(57) ABSTRACT

A human knee prosthetic implant having a tibia component forming first and second medial concave surfaces and first and second lateral concave surfaces, and a femur component forming first and second medial convex surfaces and first and second lateral convex surfaces. The tibia and femur surfaces are formed to provide contact interaction in full extension, a mid flexion range and in a state of full flexion of the knee prosthetic implant.

8 Claims, 27 Drawing Sheets

(56) References Cited

U.S. PATENT DOCUMENTS

| | | |
|---|---|---|
| 8,273,132 B2 | 9/2012 | Masini |
| 8,337,564 B2 | 12/2012 | Shah et al. |
| 8,403,992 B2 | 3/2013 | Otto et al. |
| 8,409,293 B1 | 4/2013 | Howard et al. |
| 8,647,389 B2 | 2/2014 | Otto et al. |
| 8,808,387 B2 | 8/2014 | Hawkins et al. |
| 2005/0154472 A1 | 7/2005 | Afriat |
| 2009/0036992 A1 | 2/2009 | Tsakonas |
| 2009/0319048 A1 | 12/2009 | Shah et al. |
| 2010/0016977 A1* | 1/2010 | Masini .................... A61F 2/385 623/20.21 |
| 2010/0036499 A1 | 2/2010 | Pinskerova |
| 2010/0161067 A1* | 6/2010 | Saleh ....................... A61F 2/38 623/20.31 |
| 2010/0191341 A1 | 7/2010 | Byrd |
| 2011/0022179 A1 | 1/2011 | Andriacchi et al. |
| 2011/0125275 A1 | 5/2011 | Lipman et al. |
| 2013/0204382 A1 | 8/2013 | Walker |
| 2017/0189195 A1* | 7/2017 | Blaha .................... A61F 2/3886 |

OTHER PUBLICATIONS

International Preliminary Report on Patentability dated Jan. 23, 2018.
Partial Supplemental European Search Report for EP 16882634.5-1122/3397200, dated Oct. 1, 2019 (16 pages).

\* cited by examiner

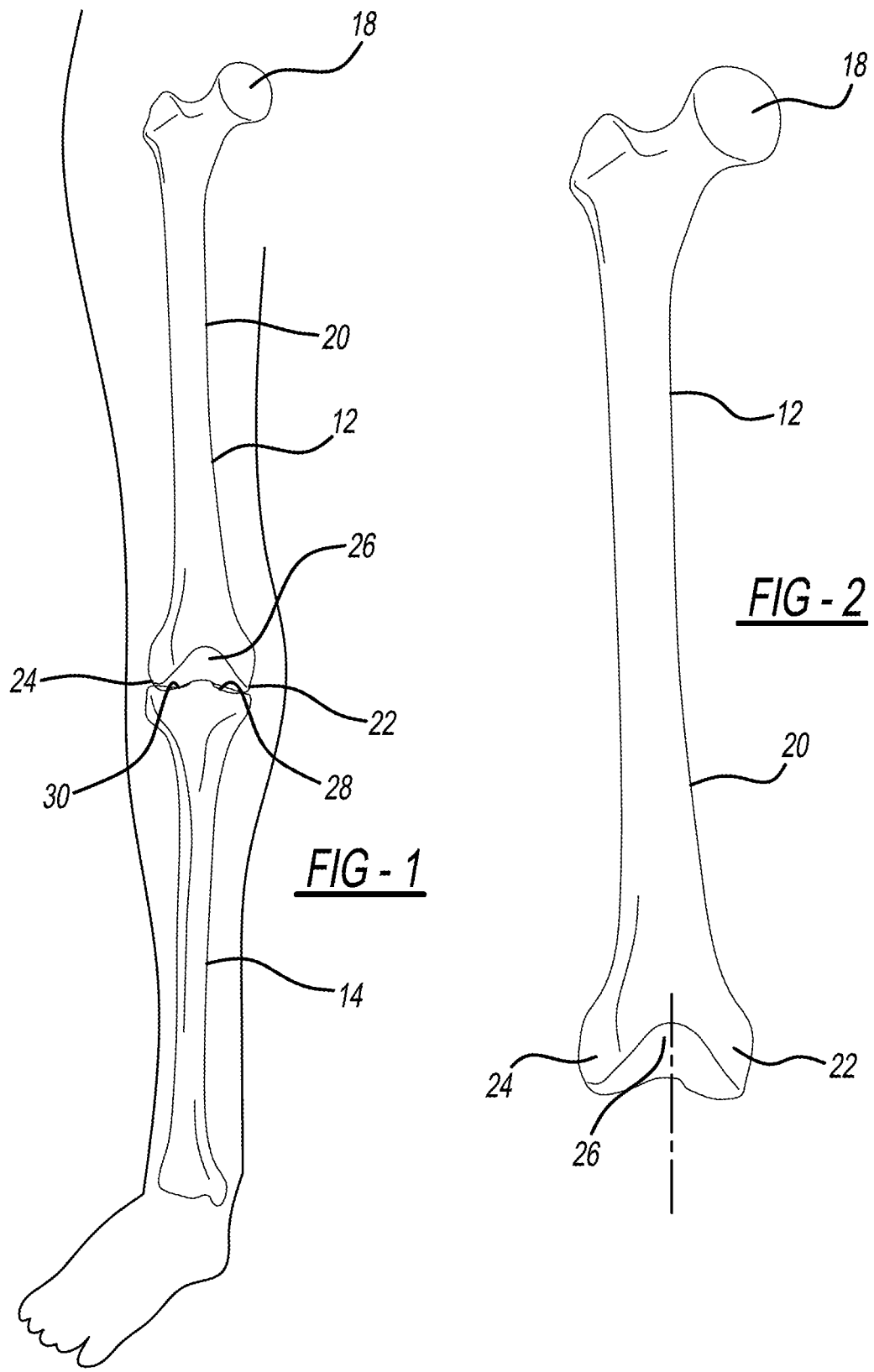

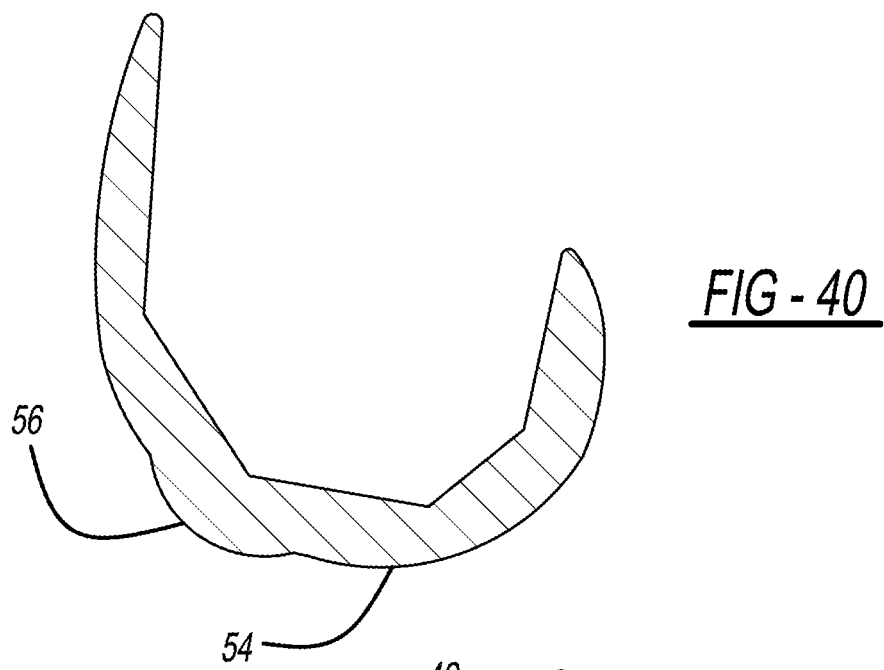
FIG - 40
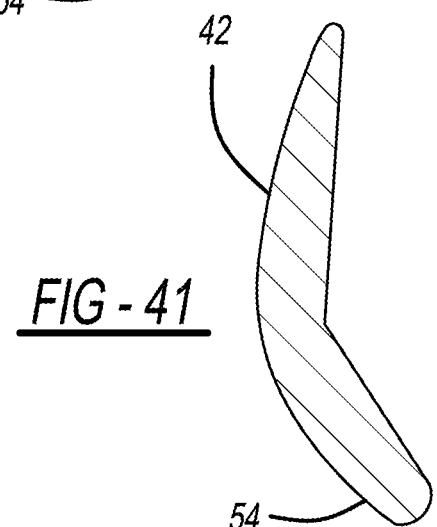
FIG - 41
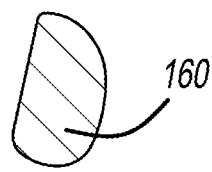
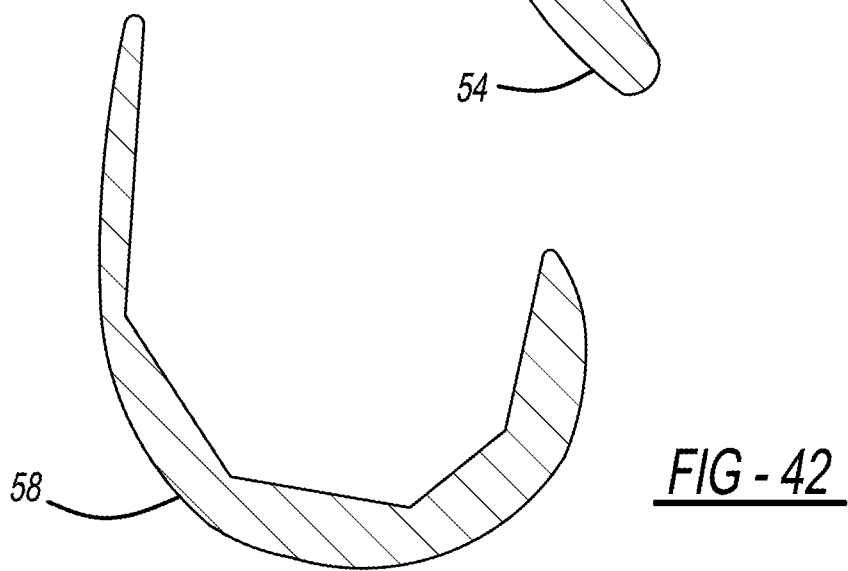
FIG - 42

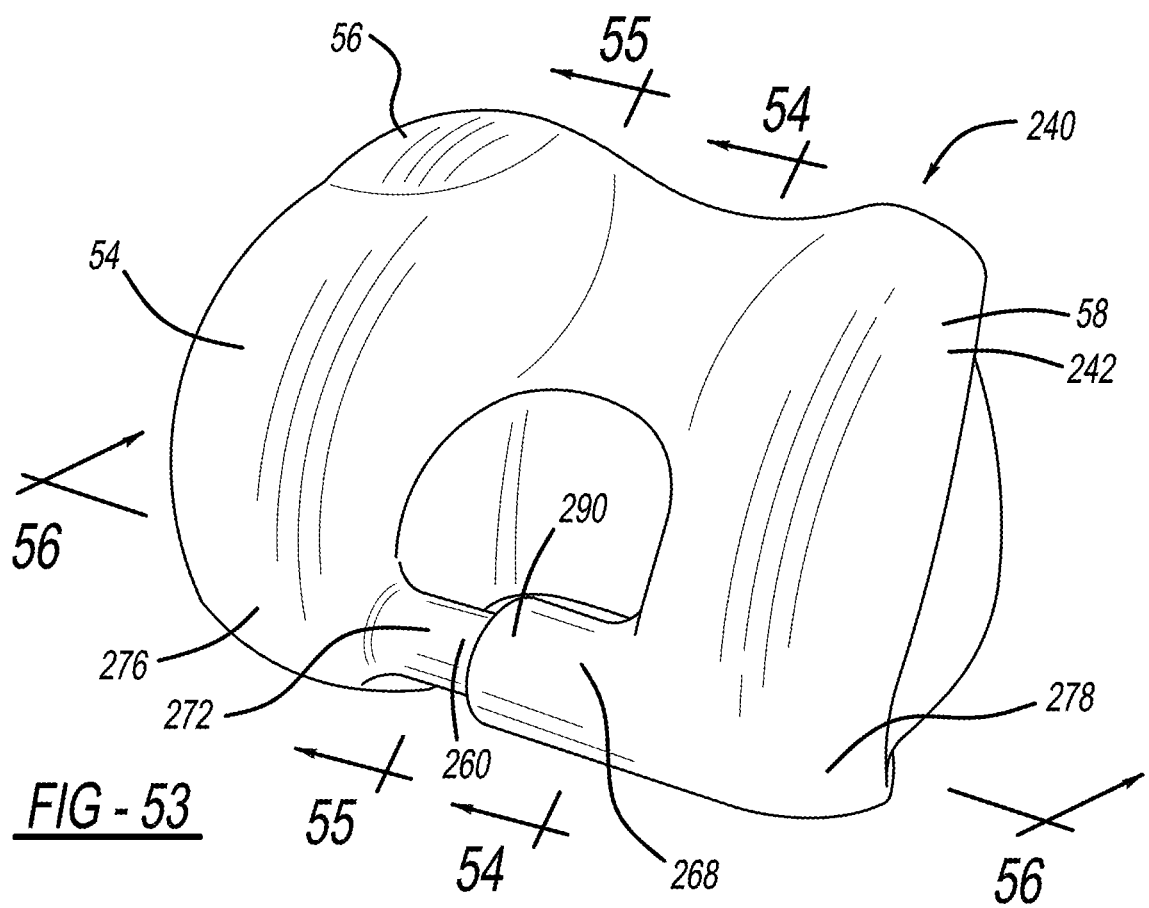
FIG-53
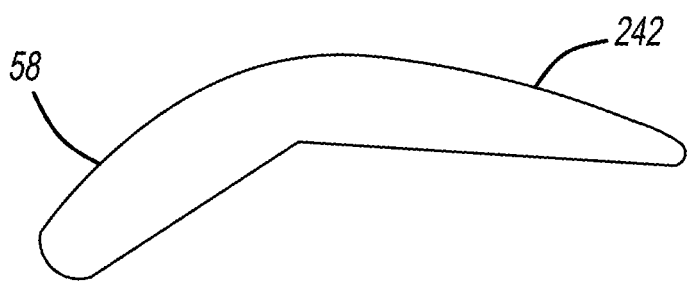
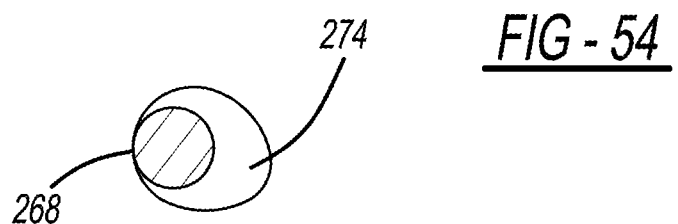
FIG-54

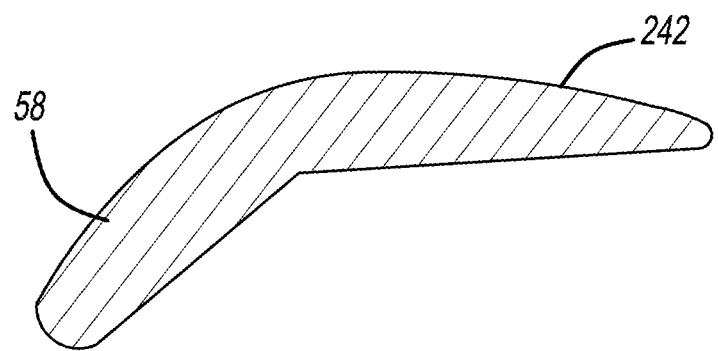
FIG - 55
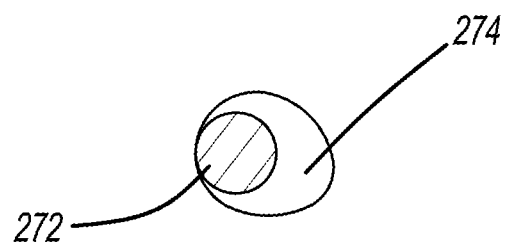
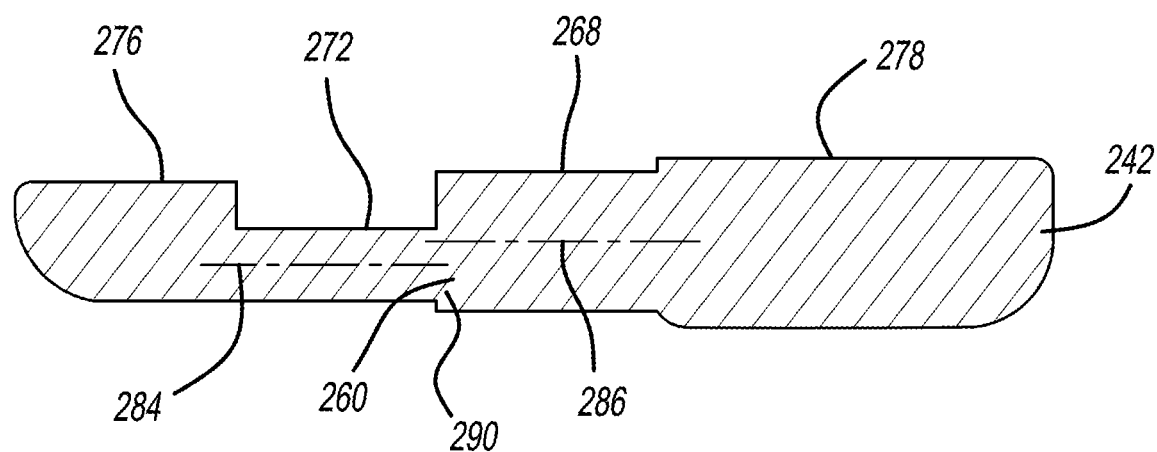
FIG - 56

KNEE PROSTHETIC IMPLANT

CROSS REFERENCE TO RELATED APPLICATION

This application is a 35 U.S.C. § 371 national phase of PCT International Application No. PCT/US2016/069088, filed Dec. 29, 2016, which claims the benefit of priority under 35 U.S.C. § 119 to U.S. Provisional Application No. 62/272,962, filed Dec. 30, 2015, the contents of which are incorporated herein by reference in their entirety.

FIELD OF THE INVENTION

This invention relates to a knee prosthetic implant for use in human total knee replacement procedures.

BACKGROUND

Due to increases in medical knowledge, and significant advancements in surgical techniques, the design and material selections for knee prosthetic joint implants and procedures for total knee arthroplasty (TKA) are changing. The increase in middle-aged and elderly persons occasioned by the "baby boom", coupled with the desire of those persons to maintain an active lifestyle has led not only to the procedures becoming more frequent but for increased demand for more normal function of the artificial joints.

The design of knee prosthetic implants has seen considerable change since its inception based primarily on a better understanding of the motion and stability of the natural knee. Initially it was thought that the articulation of a human knee could be adequately mimicked by a prosthetic implant designed as a mechanical hinge that allowed flexion-extension rotation about a single axis. Such devices suffered significant limitations, both in the range of motion of the patient's knee joint but also in breakage of the mechanism. Analysis of human knees in living patients using MRI analysis and the study of cadaver knee joints have added significantly to the understanding of the kinematic and stability behavior of the living knee. Most significant is the understanding that during the majority of flexion, the medial compartment of the knee (medial femoral condyle, medial meniscus and tibial plateau) moves largely as a simple ball-in-socket joint, whereas the lateral compartment (lateral femoral condyle, lateral meniscus and lateral tibial plateau) moves such that the contact point changes from anterior to posterior (front to back) in an arcuate path dependent largely on the longitudinal rotation of the tibia beneath the femur. Thus the contact area or point (imaginary point at the center of contact pressure) between the medial condyle of the femur and the medial tibia remains almost stationary while the lateral condyle contact point on the lateral tibia moves during activity. The behavior of the knee in the terminal 20 degrees of extension and after 115 degrees of flexion differs from the motion in the mid-range of motion. In full extension, a cam-like effect of the distal medial articular surface moves the femur away from the tibial surface, tightens the medial and lateral collateral ligaments, and creates an external rotation of the tibia called "screw-home". Beyond 115 degrees of flexion the lateral tibial contacts the posterior lateral tibial surface in a rolling and sliding motion that moves the lateral femoral condyle off the back of the tibia ("roll off") and allows full flexion while decompressing the contents of the popliteal fossa. Thus the knee has three ranges of motion: full-extension, midrange flexion, and full-flexion.

Stability at the medial side of the knee is provided by the conformity between the femoral condyle and the concave tibial surface with the attached medial meniscus such that the construct resists anterior-posterior (AP) displacement, while the lateral side of the knee with its convex surface and less firmly attached meniscus does not provide a high degree of AP constraint but is free to move in and anterior-posterior manner with knee flexion. This kinematic behavior provides that at the medial interface acts as the center or rotation for internal/external rotation of the tibia while the lateral femoral condyle moves anteriorly and posteriorly. An elongated distal contour of the medial femoral condyle creates the cam-effect and screw-home motion at the last 10-15° of extension. The anterior-posterior mobility of the lateral compartment allows the unique motion in flexion beyond 115 degrees.

Knee prosthetic implants ideally seek to match the kinematic and stability behavior of a healthy living knee. Paramount is maintaining stability of the joint through the full range of motion. Currently available knee prosthetic implants rely heavily on tension in the medial and lateral collateral ligaments with or without tension in the posterior cruciate ligament to drive kinematics and stability. It is conventionally understood that adjusting (through "ligament balancing") and maintaining tension in these ligaments throughout flexion is essential to providing stability of the joint. However, in the total knee arthroplasty procedure it is difficult to achieve desired tension in these ligaments and lack of the desired tension or excessive tension leads to a result unacceptable to the patient. Insufficient ligament tension leads to joint instability and a result unacceptable in terms of function to the patient, and in extreme cases dislocation of the joint. Excessive ligament tension leads to restrictions in range of motion and the potential for ligament failure. Moreover, most designs fail to provide a full range of flexion movement because the type of stability and motion found in the normal knee (referenced above) is not provided by the articulation and ligamentous tension.

SUMMARY

The present invention, a knee prosthetic implant for total knee arthroplasty relies on the conformation of interfacing surfaces during the full range of motion (i.e., all three ranges of motion identified previously) to provide a large range of motion of the joint, and stability throughout flexion but not relying primarily on ligament tension to provide such. These features are provided through sets of cooperating convex and concave facet surfaces within the prosthesis joint compartment which cooperate in the ranges of motion.

BRIEF DESCRIPTION OF THE DRAWINGS

FIG. 1 is an anterior view of a normal human leg showing bone structures, omitting the fibula.

FIG. 2 is an anterior view of the human femur;

First Embodiment

Figure 7:
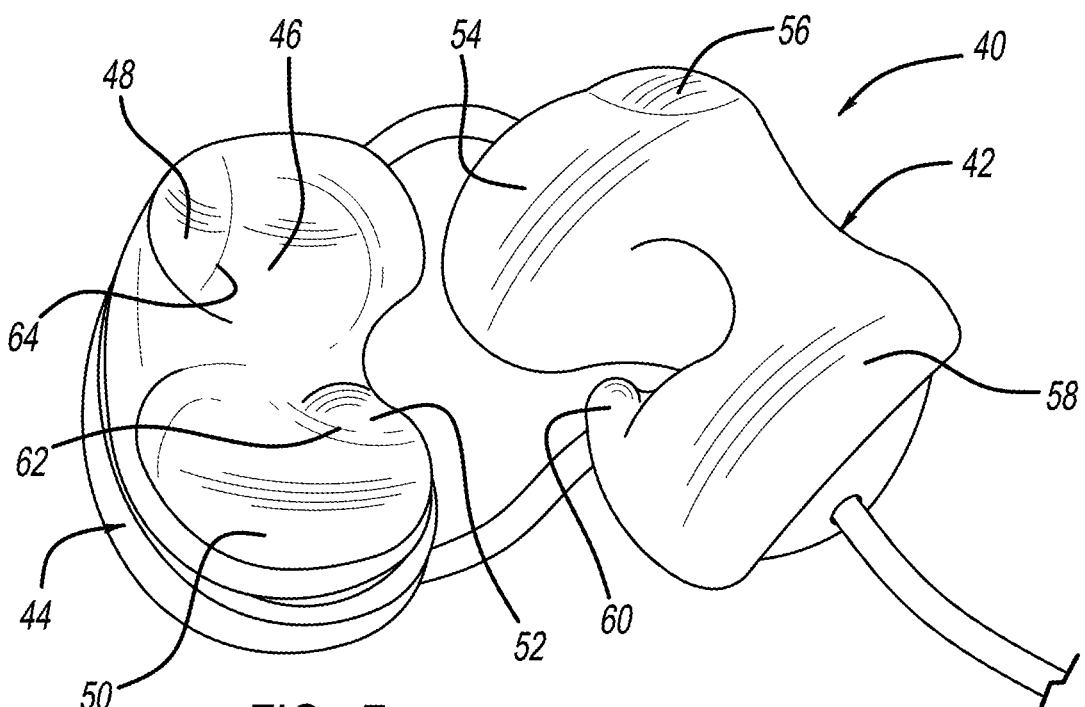
Figure 8:
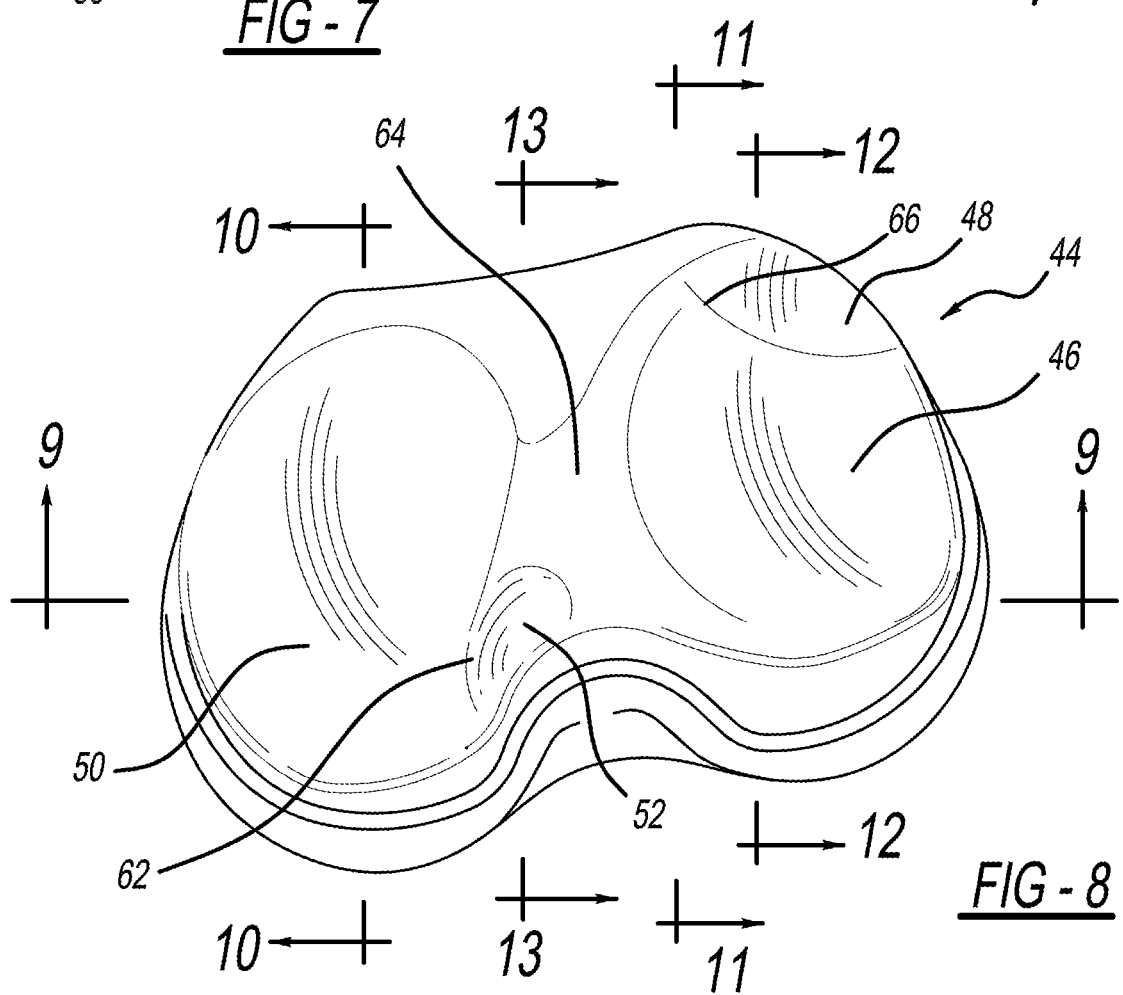
Figure 9:
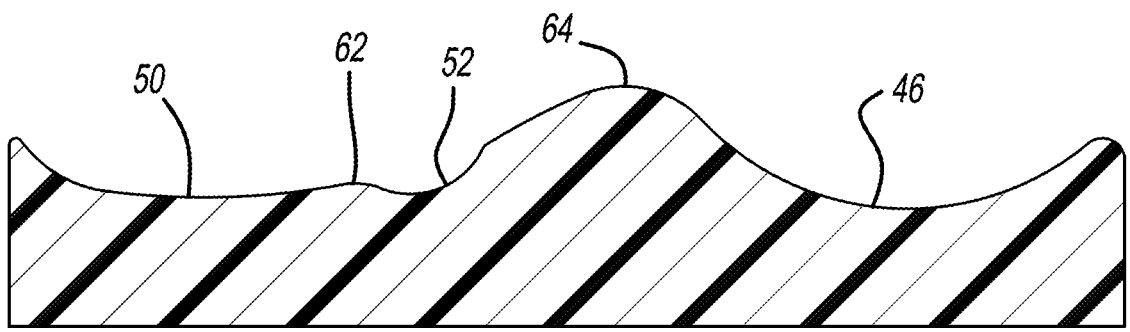
Figure 10:
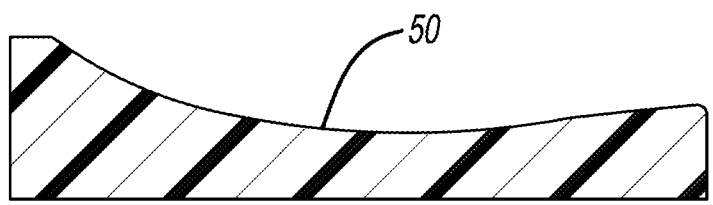
Figure 11:
Figure 12:
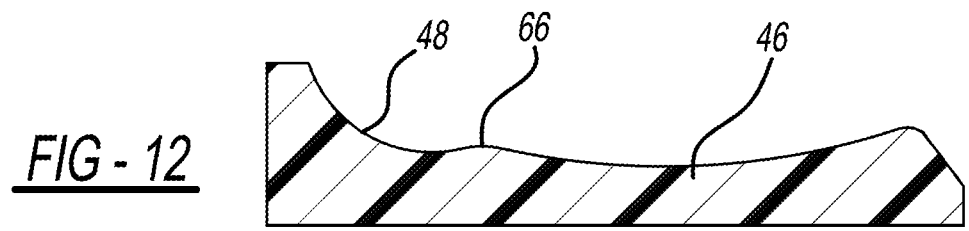
Figure 13:
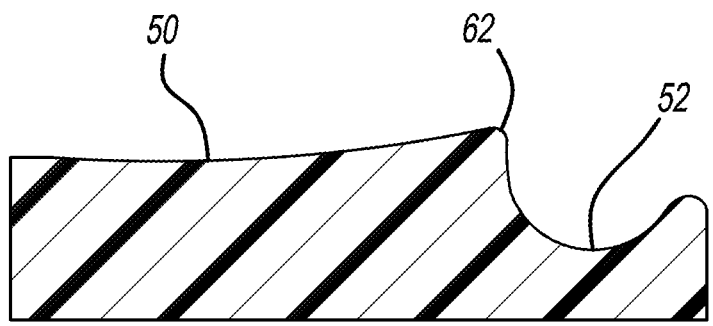
Figure 14:
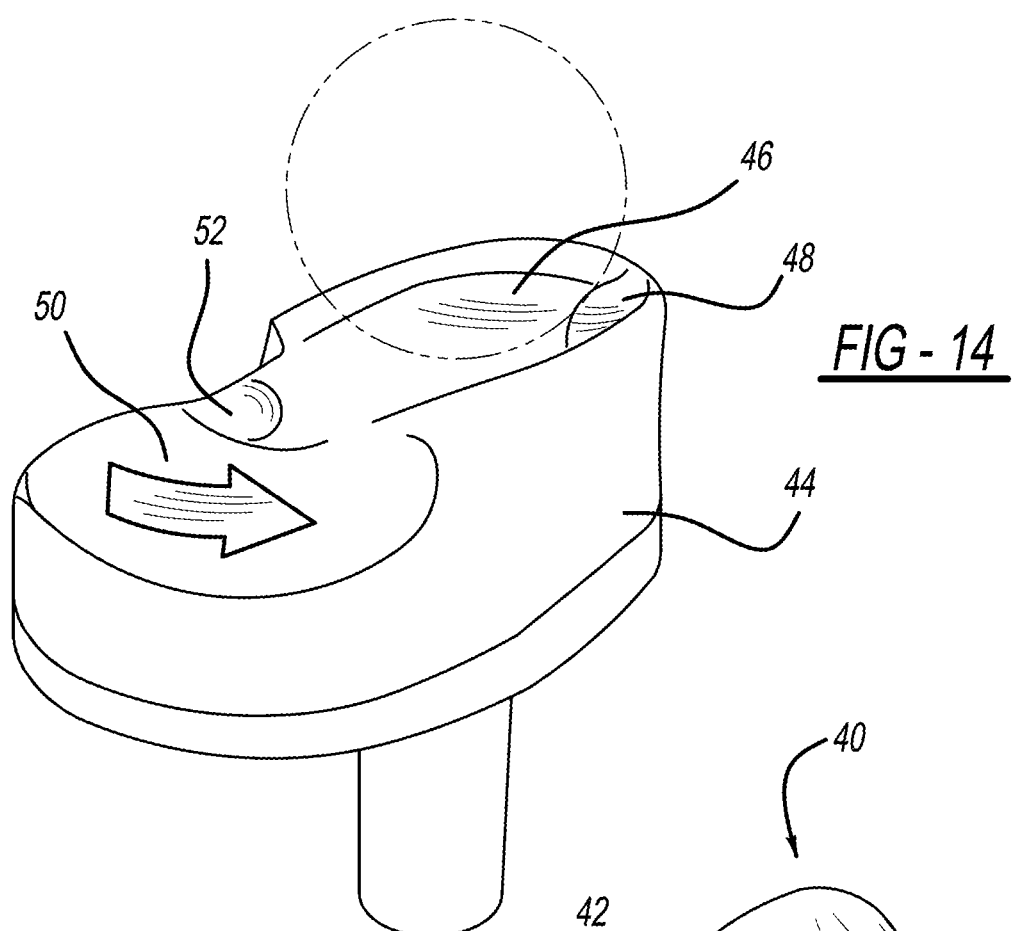
Figure 15:
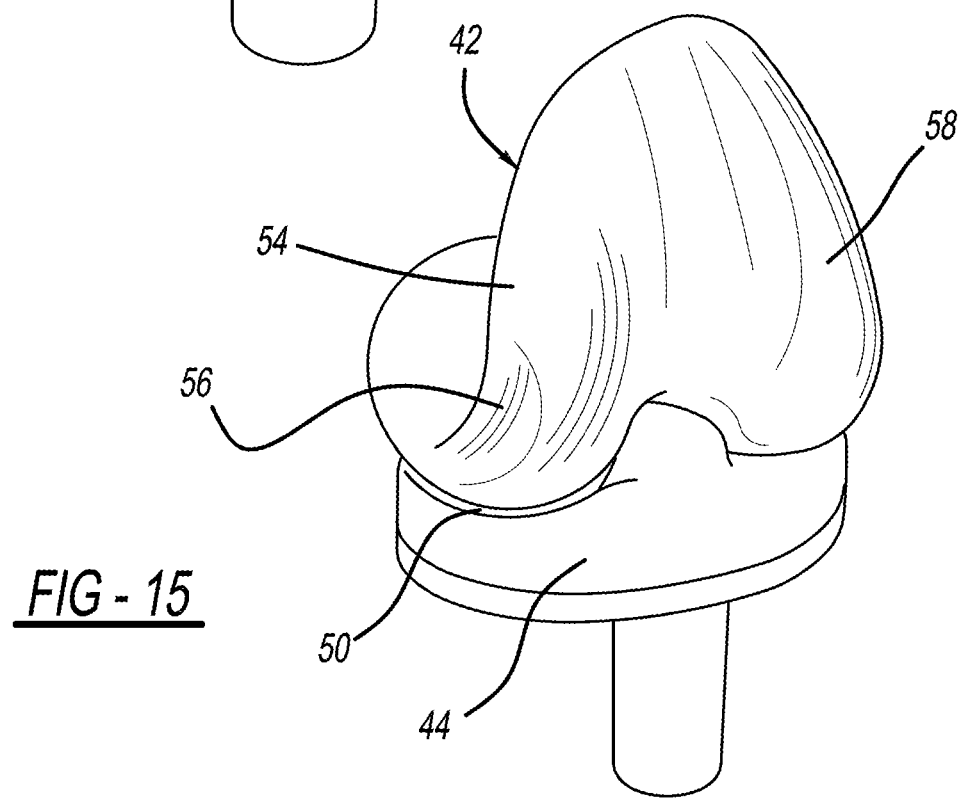
Figure 16:
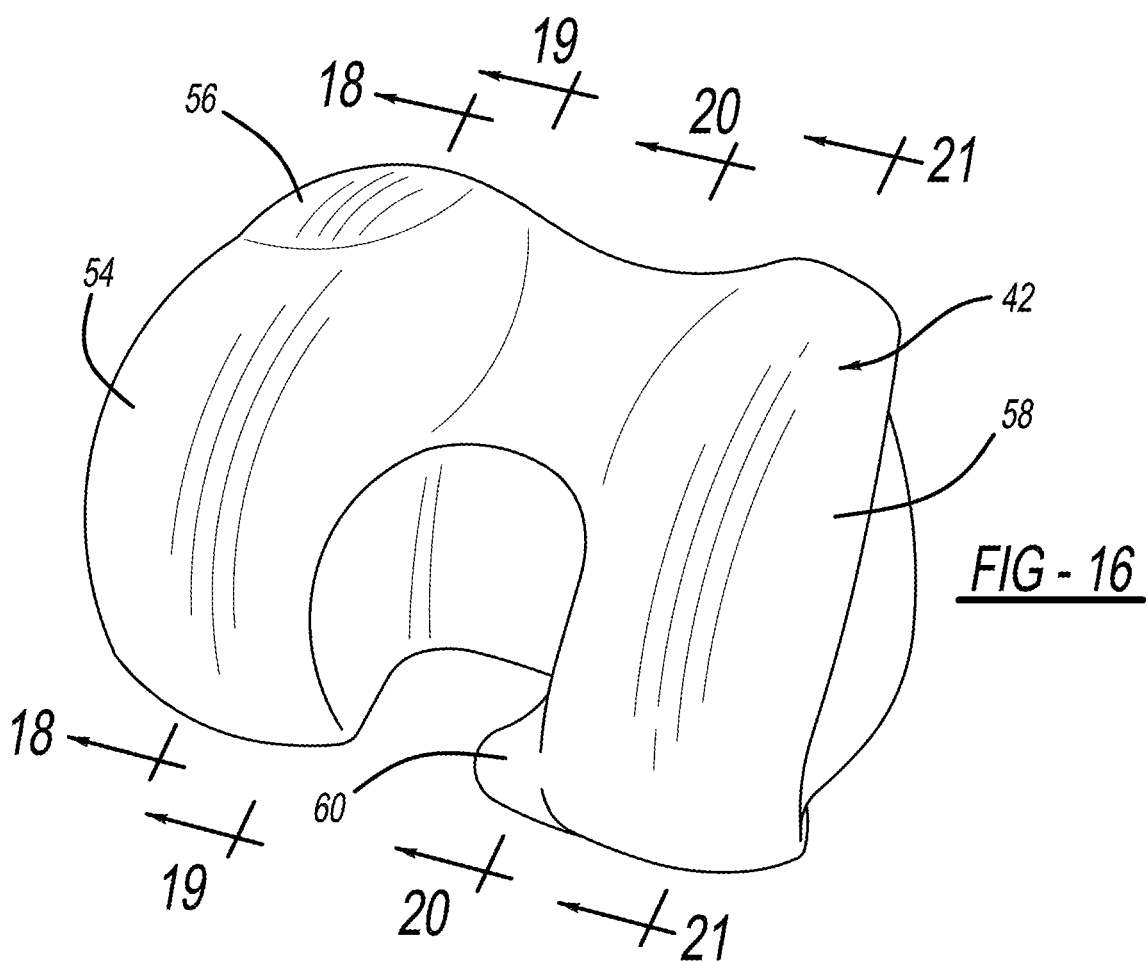
Figure 17:
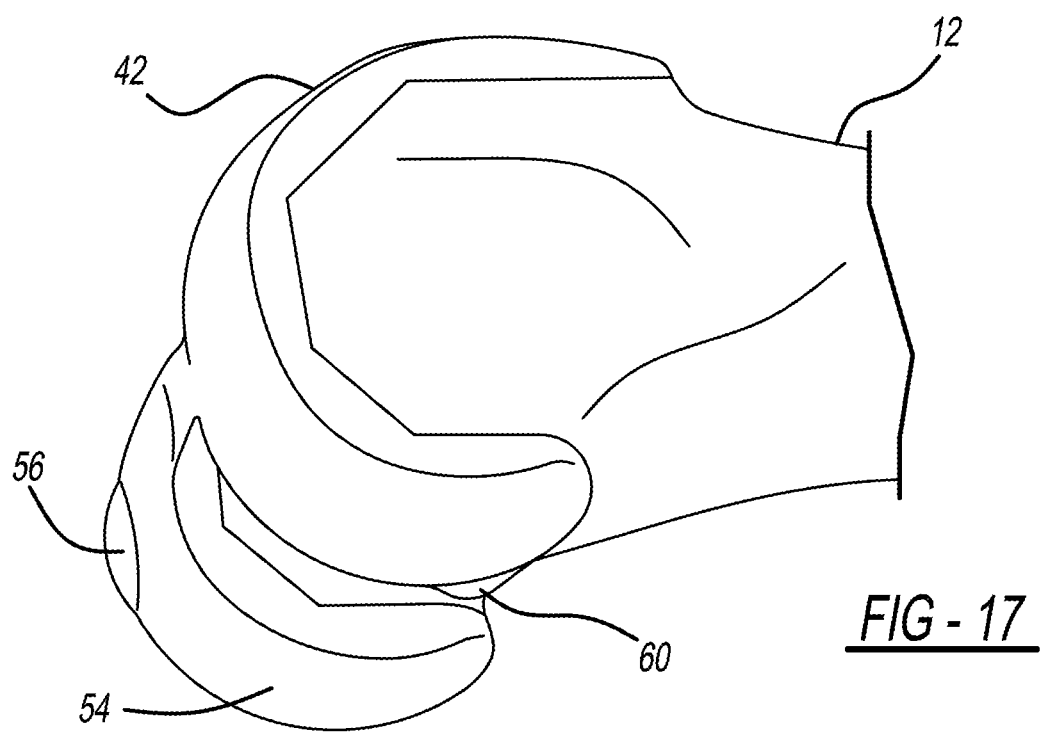
Figure 18:
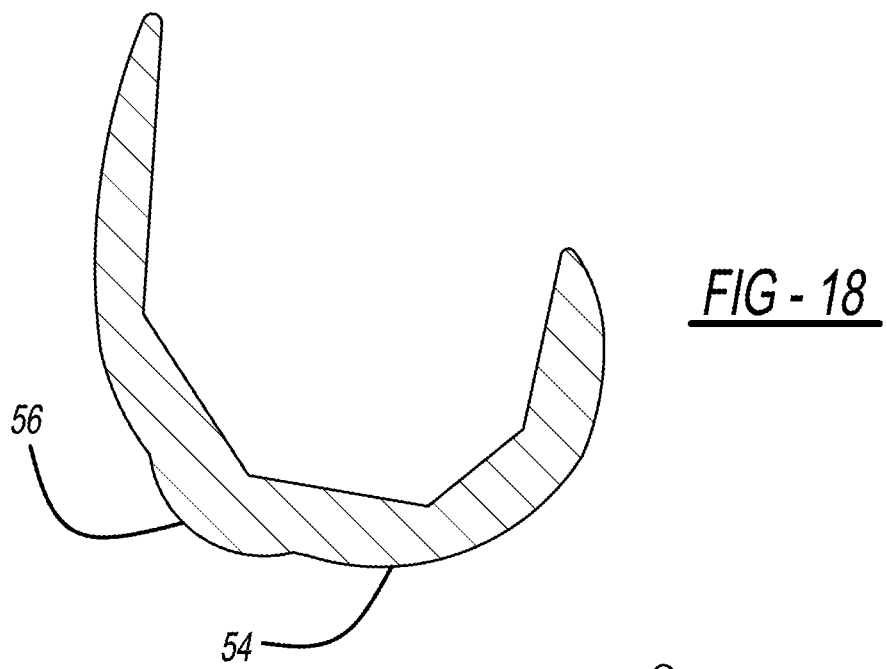
Figure 19:
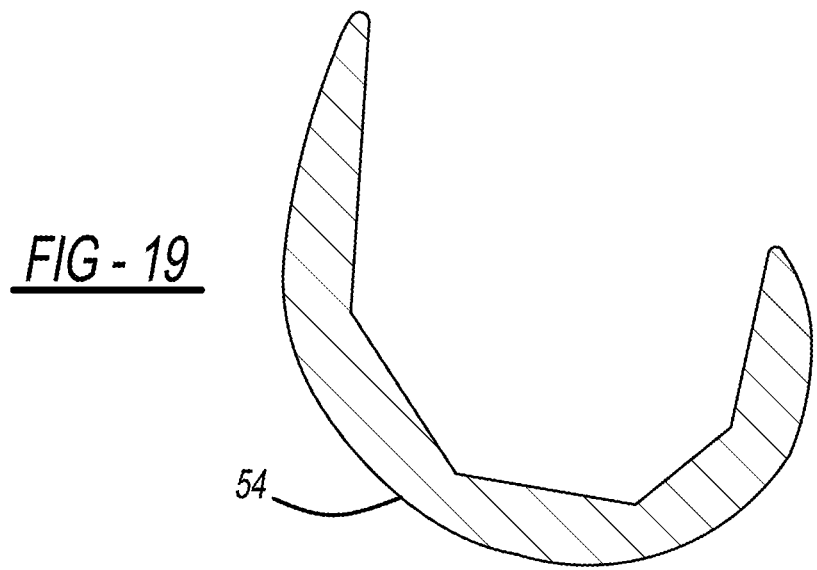
Figure 20:
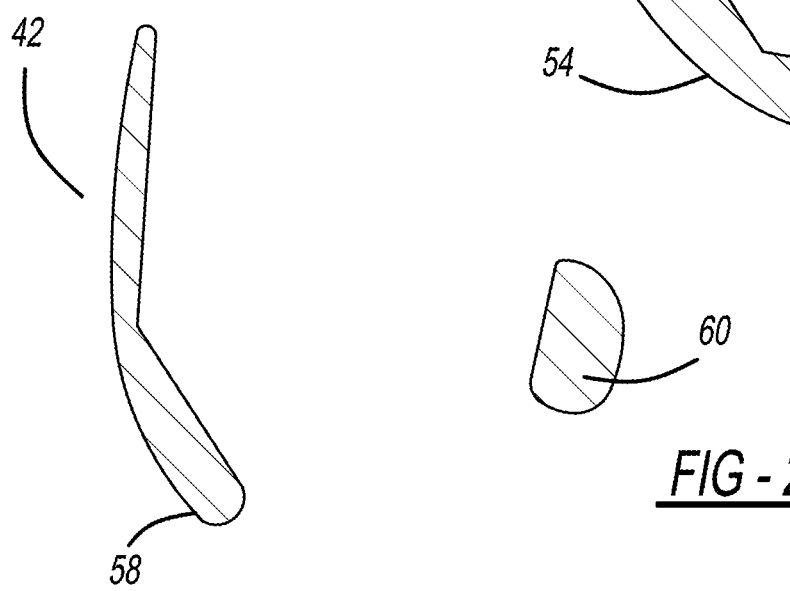
Figure 21:
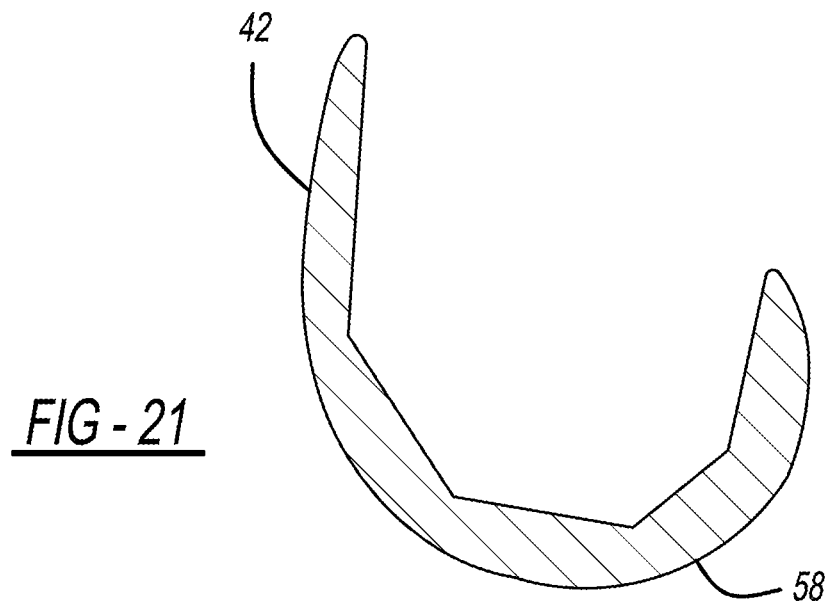
Figure 22:
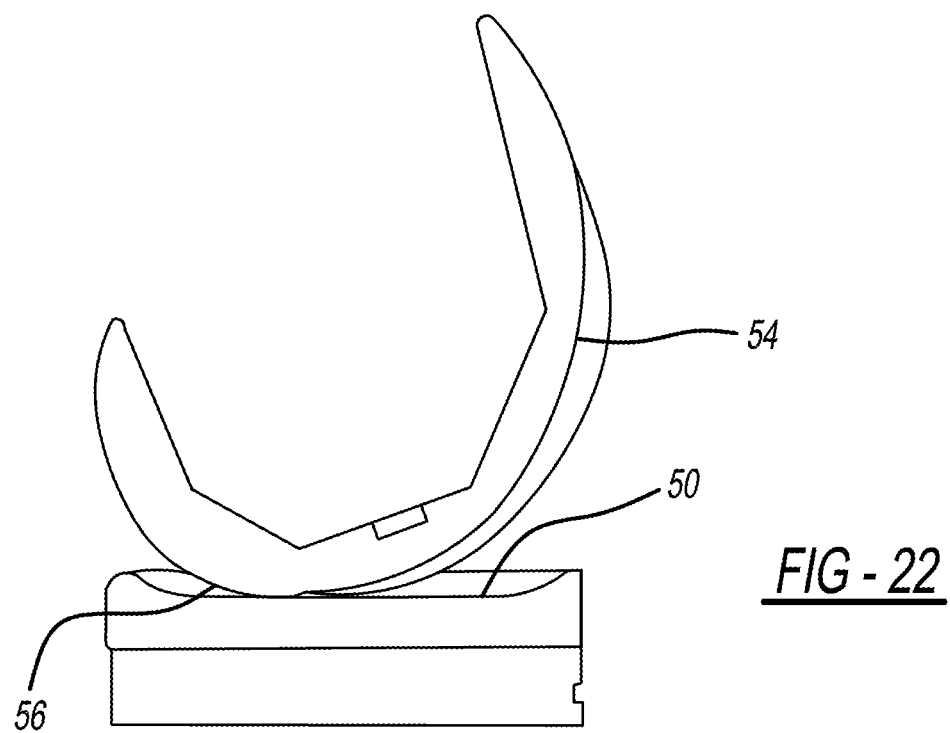
Figure 23:
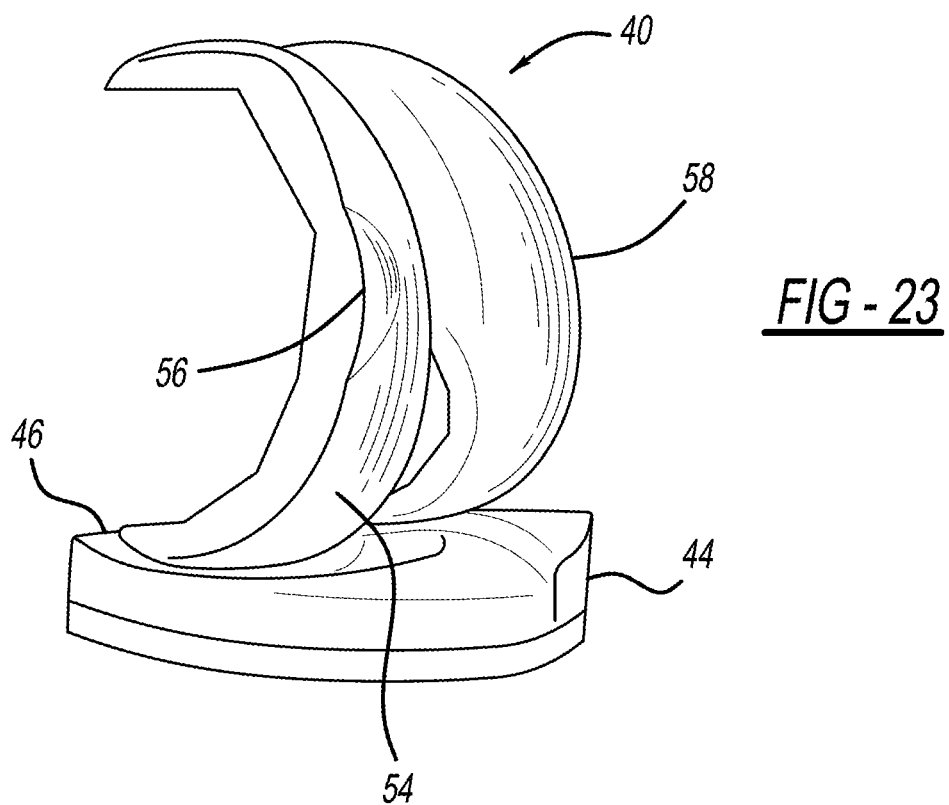
Figure 24:
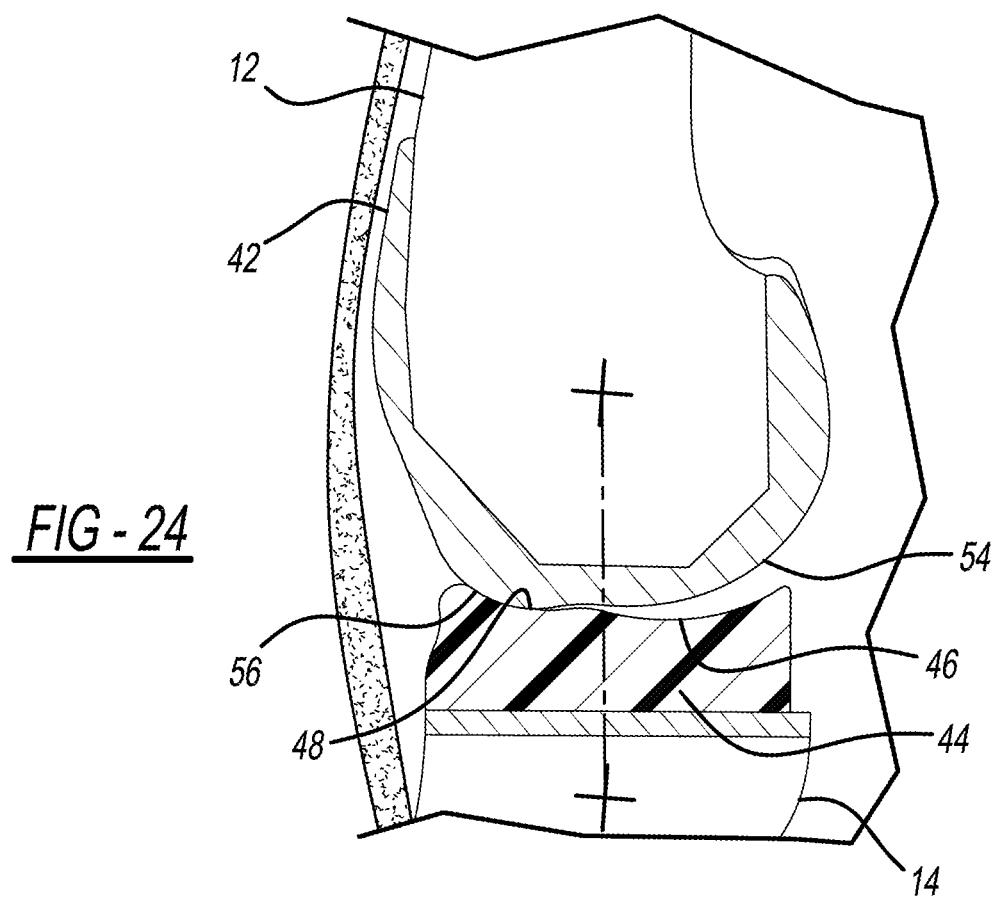
Figure 25:
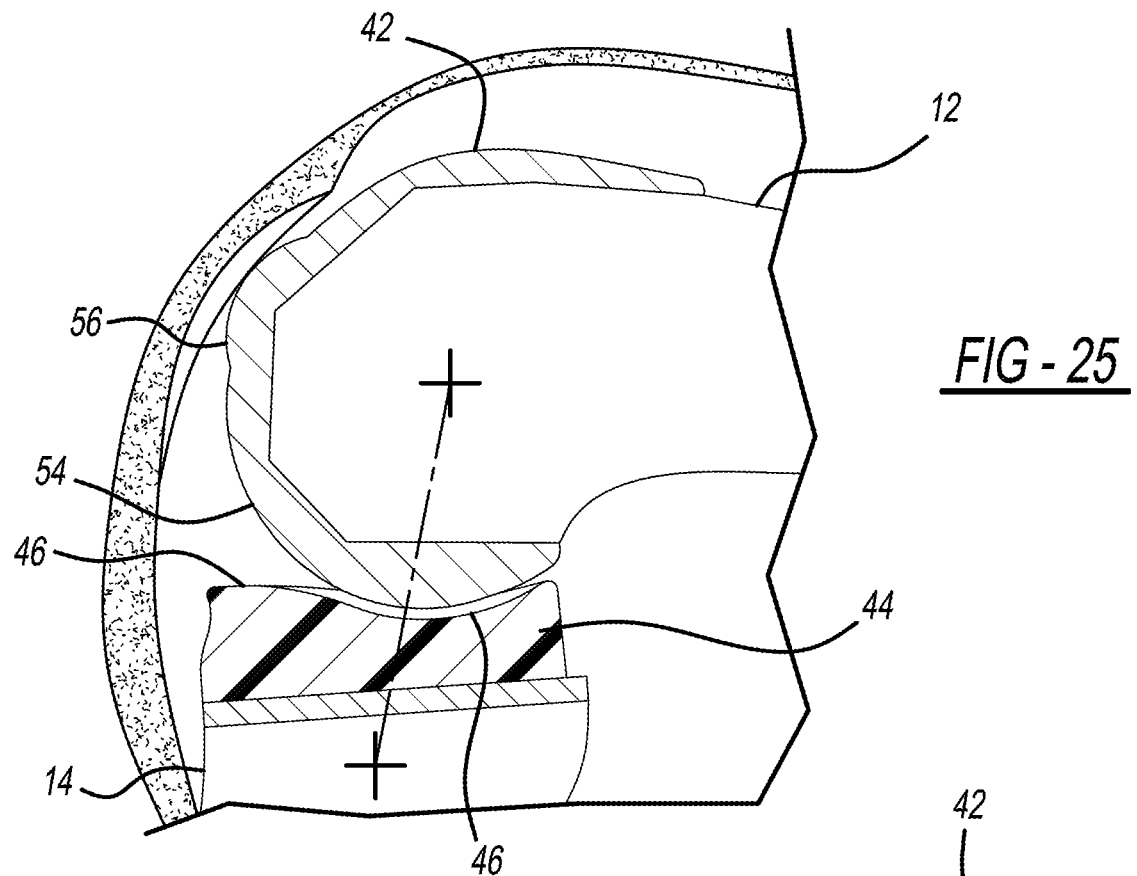
Figure 26:
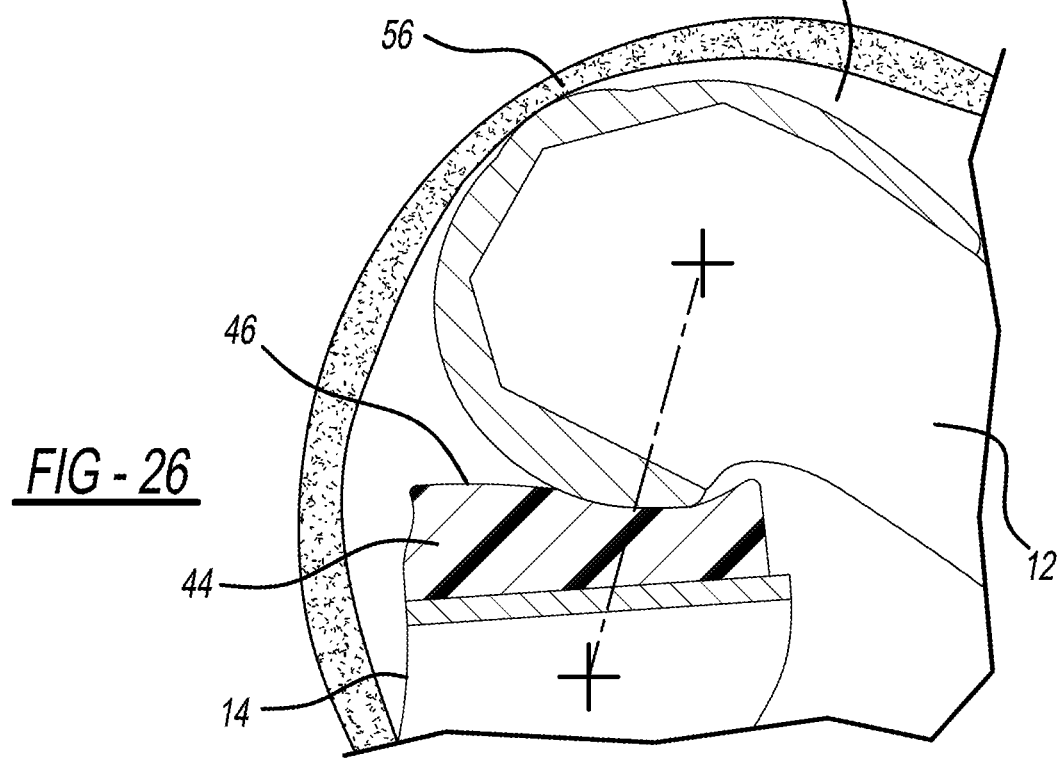
Figure 27:
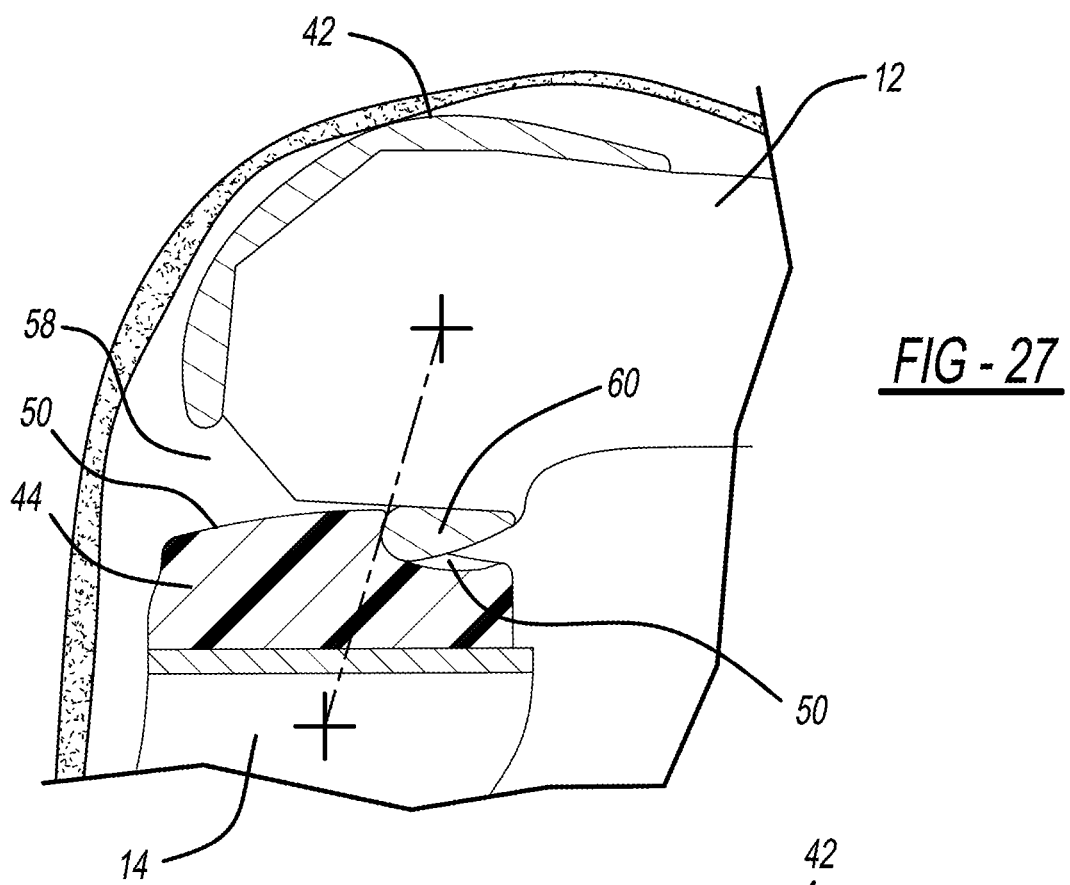
Figure 28:
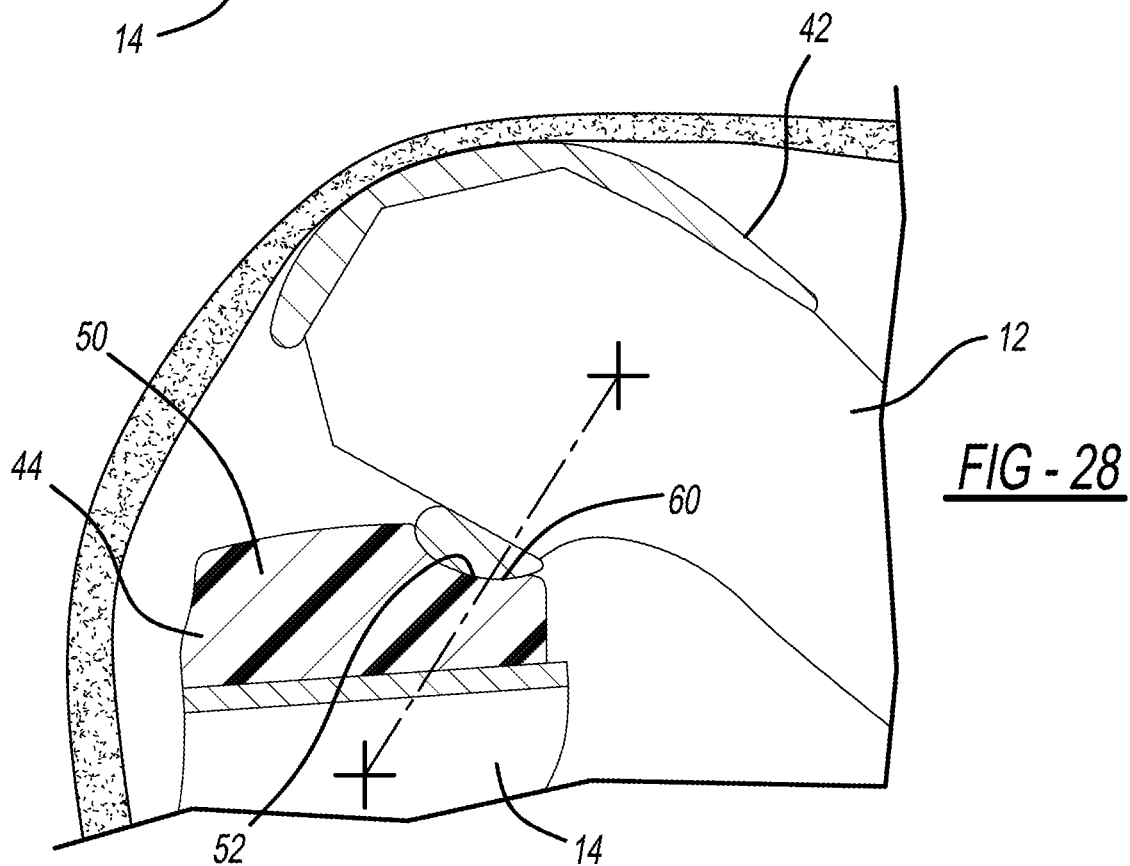

FIGS. 7-28 illustrate a total knee replacement prosthetic implant in accordance with the first embodiment of the present invention in which FIG. 7 is a pictorial view of total knee replacement prosthetic implant particularly showing the interface surfaces between the femur and tibia components;

FIG. 8 is a top view of the tibia component shown in FIG. 7;

FIG. 9 is a cross-sectional view taken along line 9-9 from FIG. 8;

FIG. 10 is a cross-sectional view taken along line 10-10 from FIG. 8;

FIG. 11 is a cross-sectional view taken along line 11-11 from FIG. 8;

FIG. 12 is a cross-sectional view taken along line 12-12 from FIG. 8;

FIG. 13 is a cross-sectional view taken along line 13-13 from FIG. 8;

FIG. 14 pictorial view of the tibia component;

FIG. 15 is a pictorial view of the femur and tibia components of the present invention shown in a conforming position;

FIG. 16 is a pictorial view of the femur implant component;

FIG. 17 is an oblique view of the femur component;

FIG. 18 is a cross-sectional view taken along line 18-18 from FIG. 16;

FIG. 19 is a cross-sectional view taken along line 19-19 from FIG. 16;

FIG. 20 is a cross-sectional view taken along line 20-20 from FIG. 16;

FIG. 21 is a cross-sectional view taken along line 21-21 from FIG. 16;

FIG. 22 is a lateral view through the first embodiment;

FIG. 23 a pictorial view of the implant components;

FIG. 24 is a sagittal section through the implanted components showing the medial interface at full extension;

FIG. 25 is a sagittal section through the medial interface of the implant components showing the joint at mid flexion;

FIG. 26 is a sagittal section through the medial compartment of the implant components shown in the joint at full flexion;

FIG. 27 is a sagittal section through the lateral interface of the implant components showing the joint at mid flexion; and FIG. 28 a sagittal section through the lateral interface of the implant components shown in the joint at full flexion.

Second Embodiment

Figure 29:
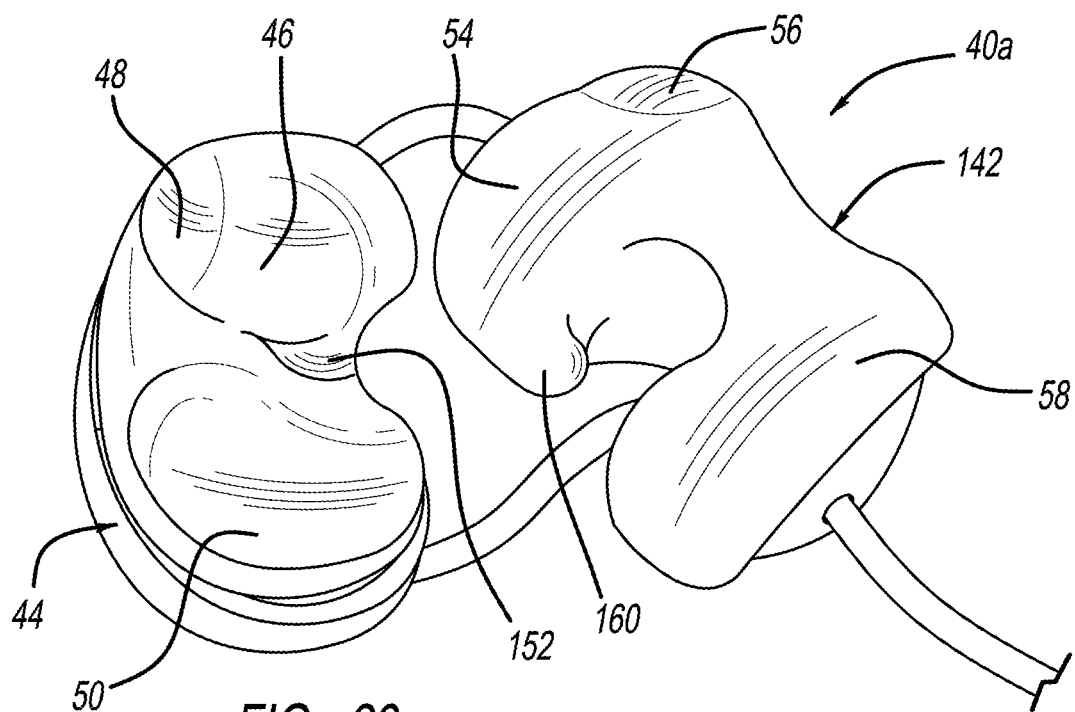
Figure 30:
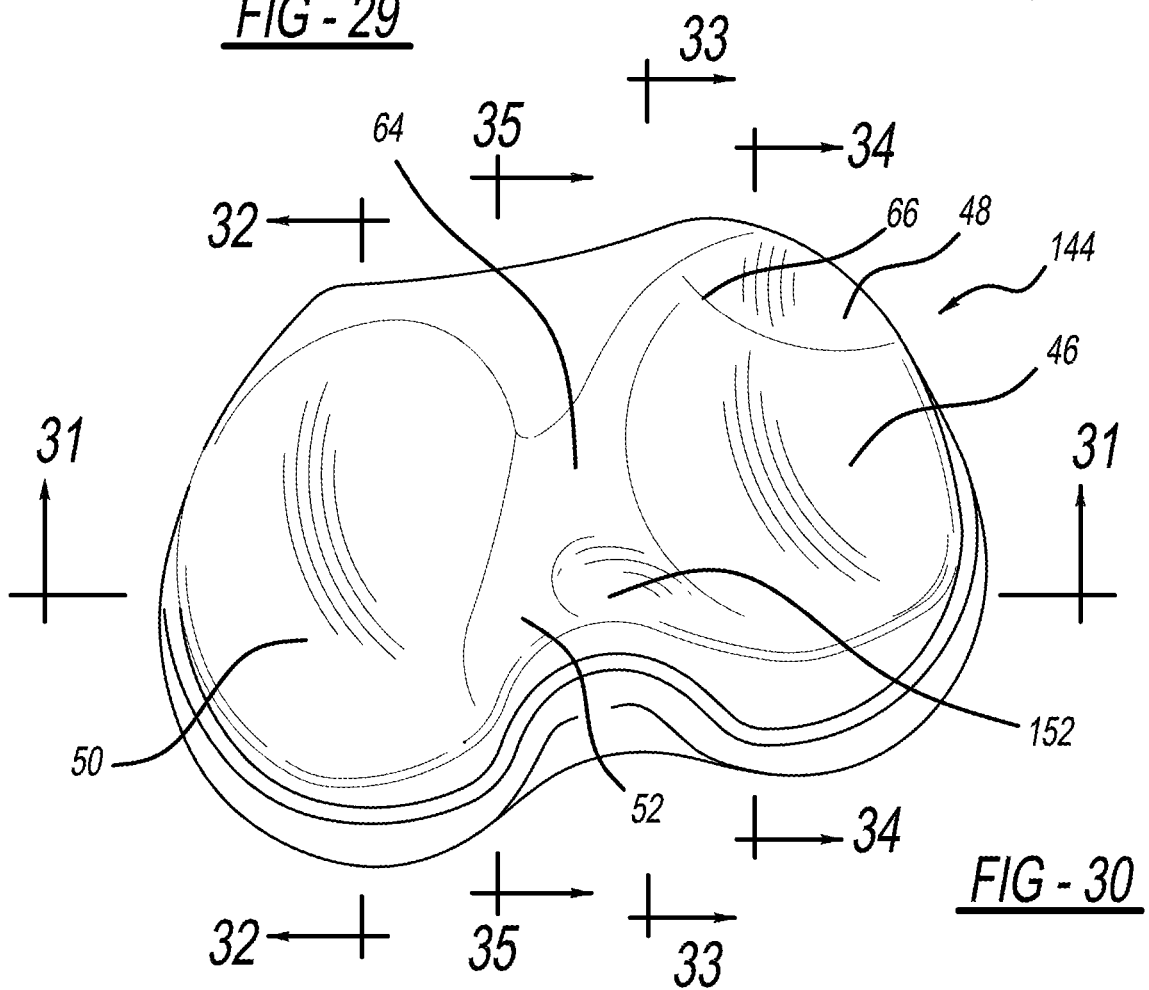
Figure 31:
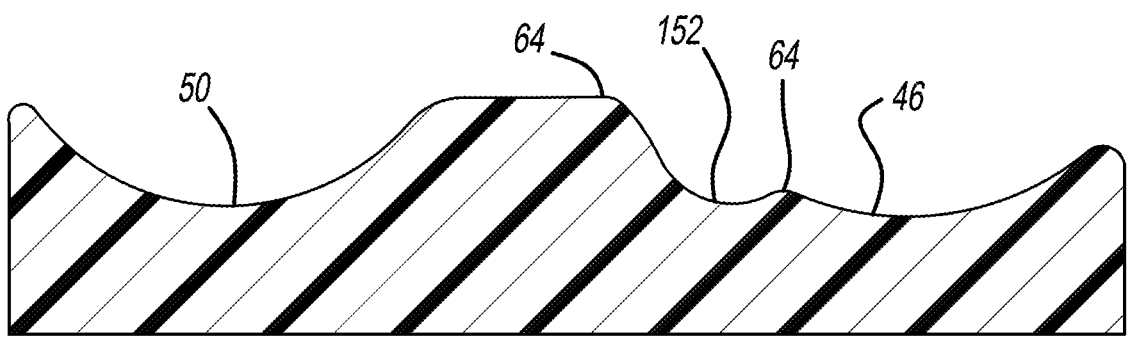
Figure 32:
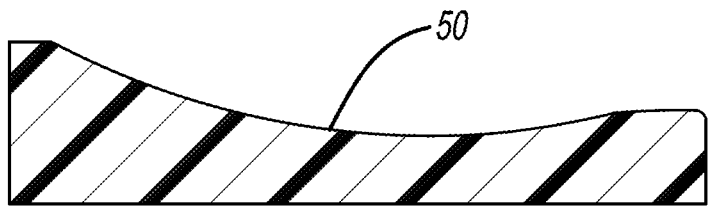
Figure 33:
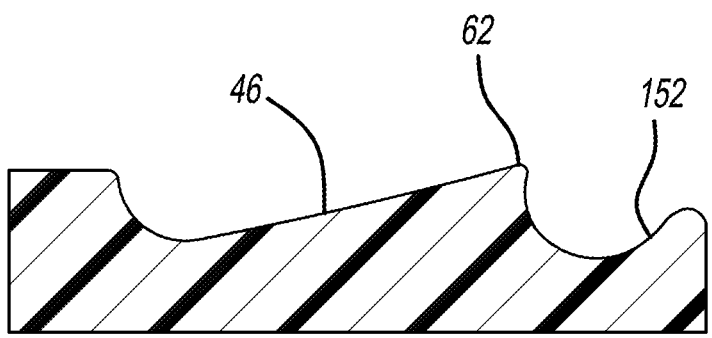
Figure 34:
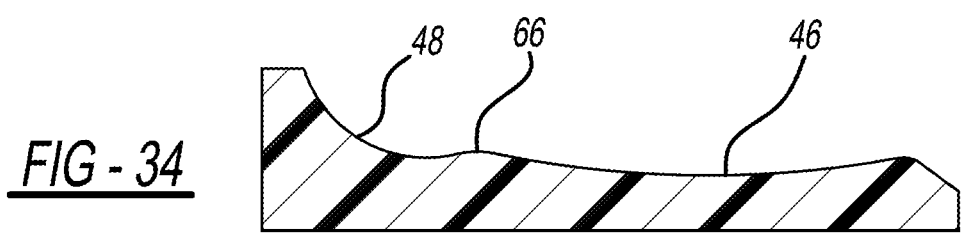
Figure 35:
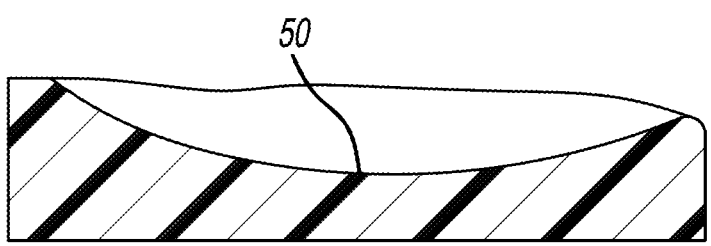
Figure 36:
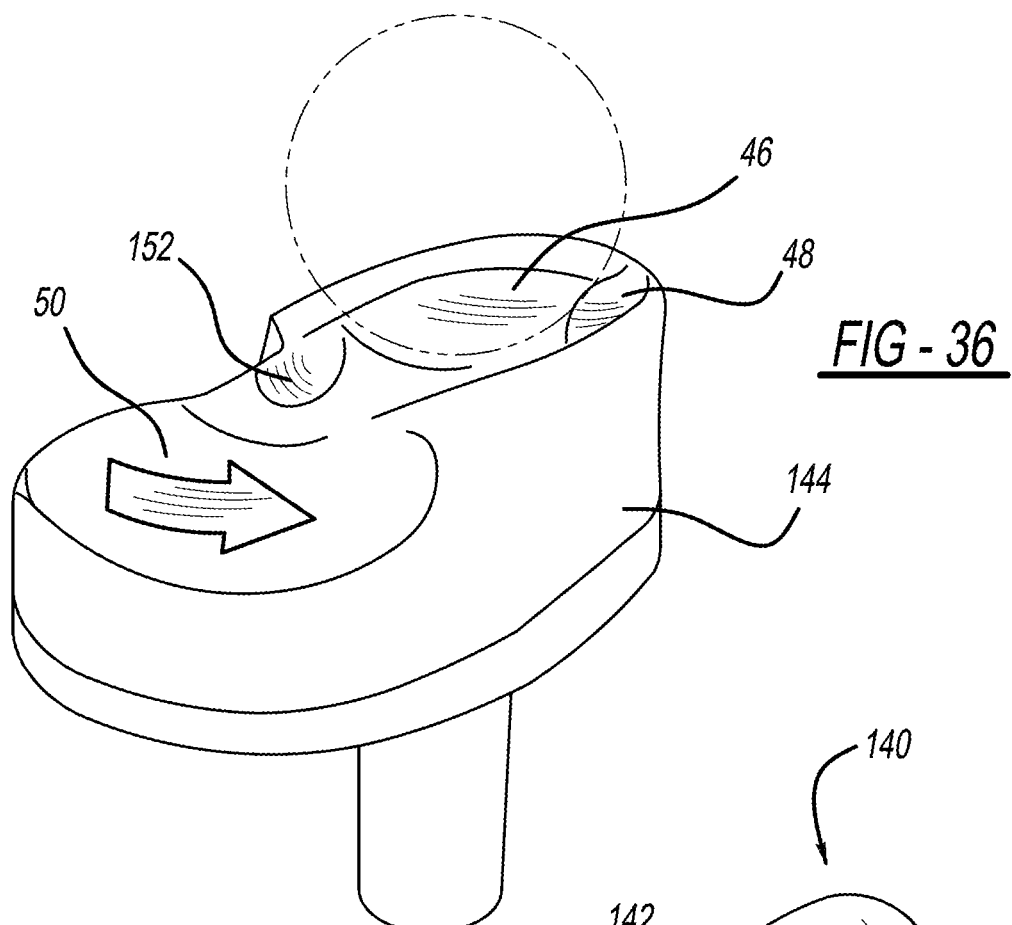
Figure 37:
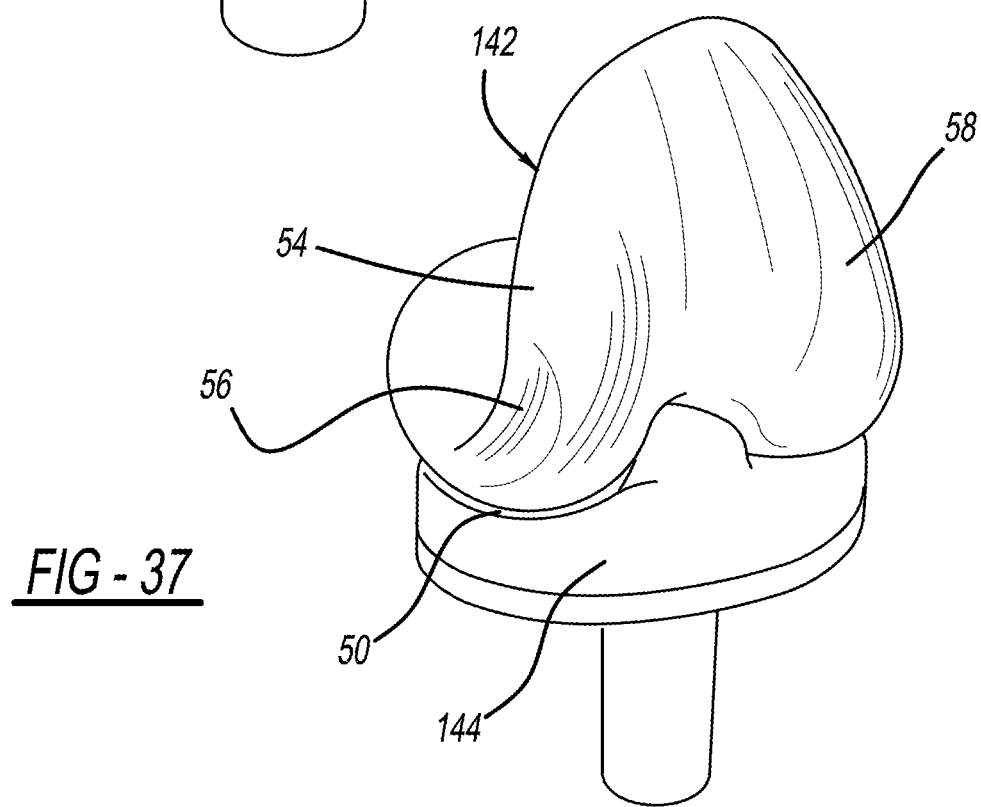
Figure 38:
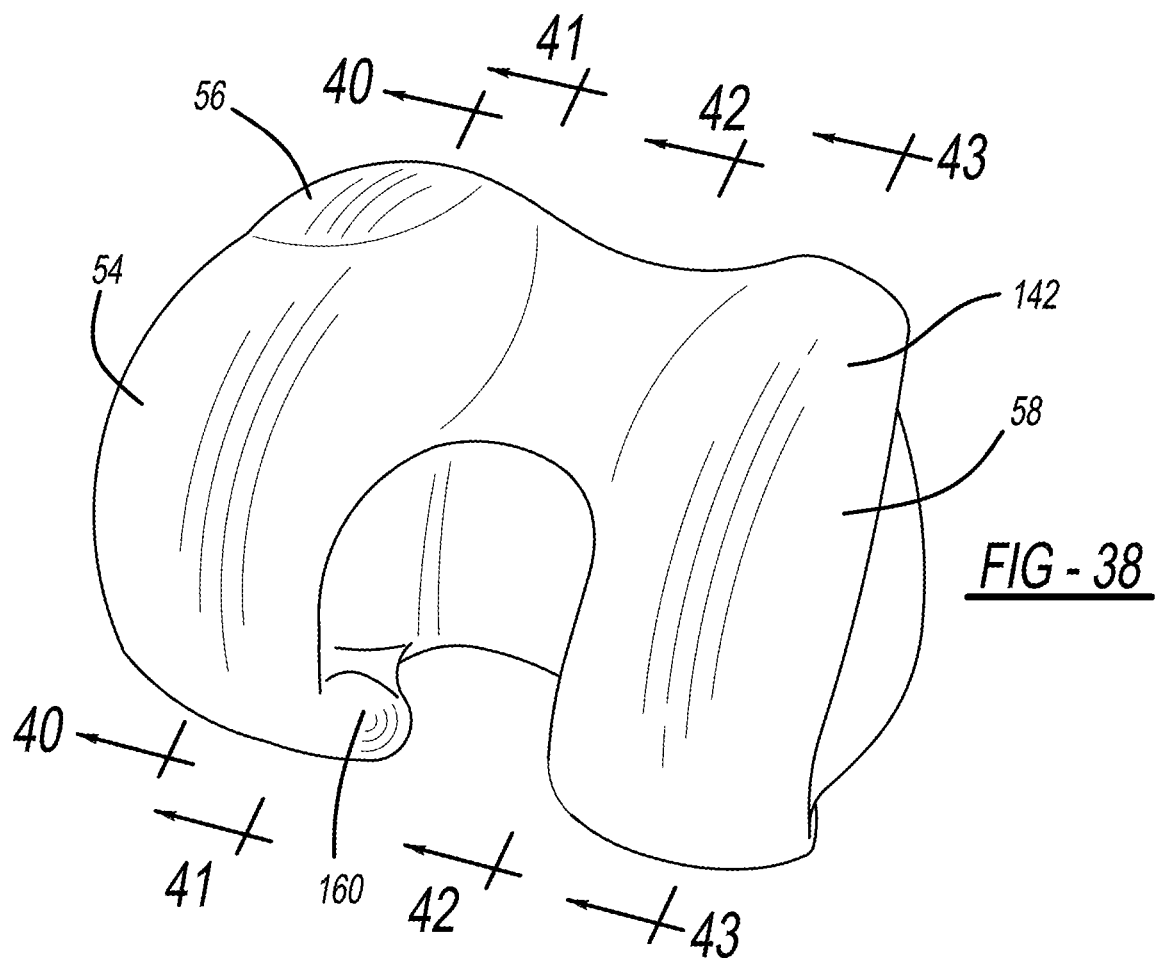
Figure 39:
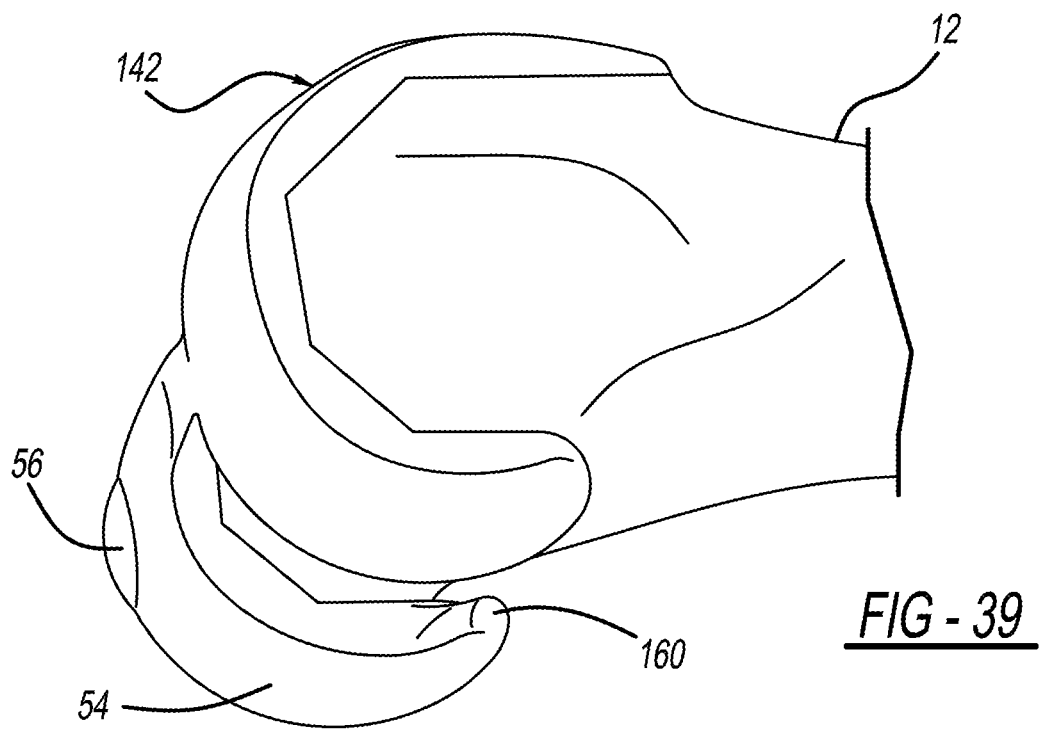
Figure 43:
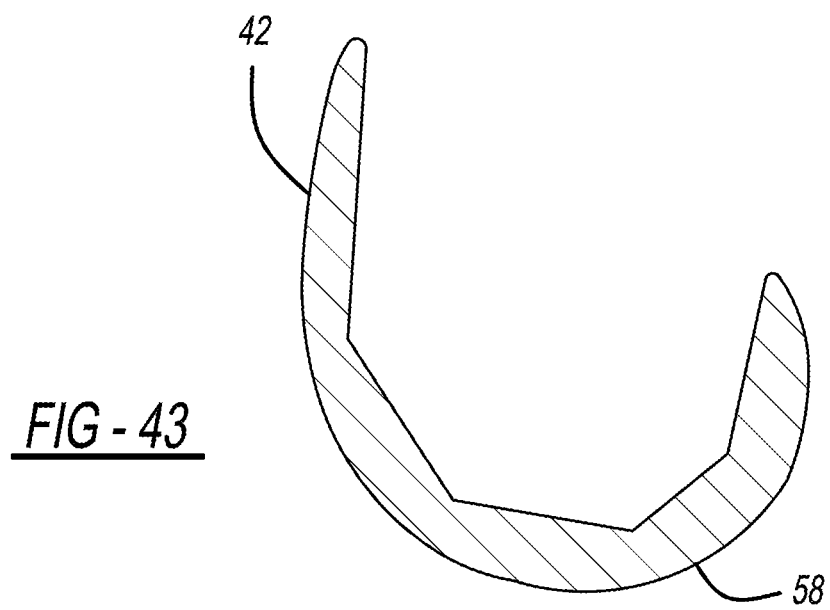
Figure 44:
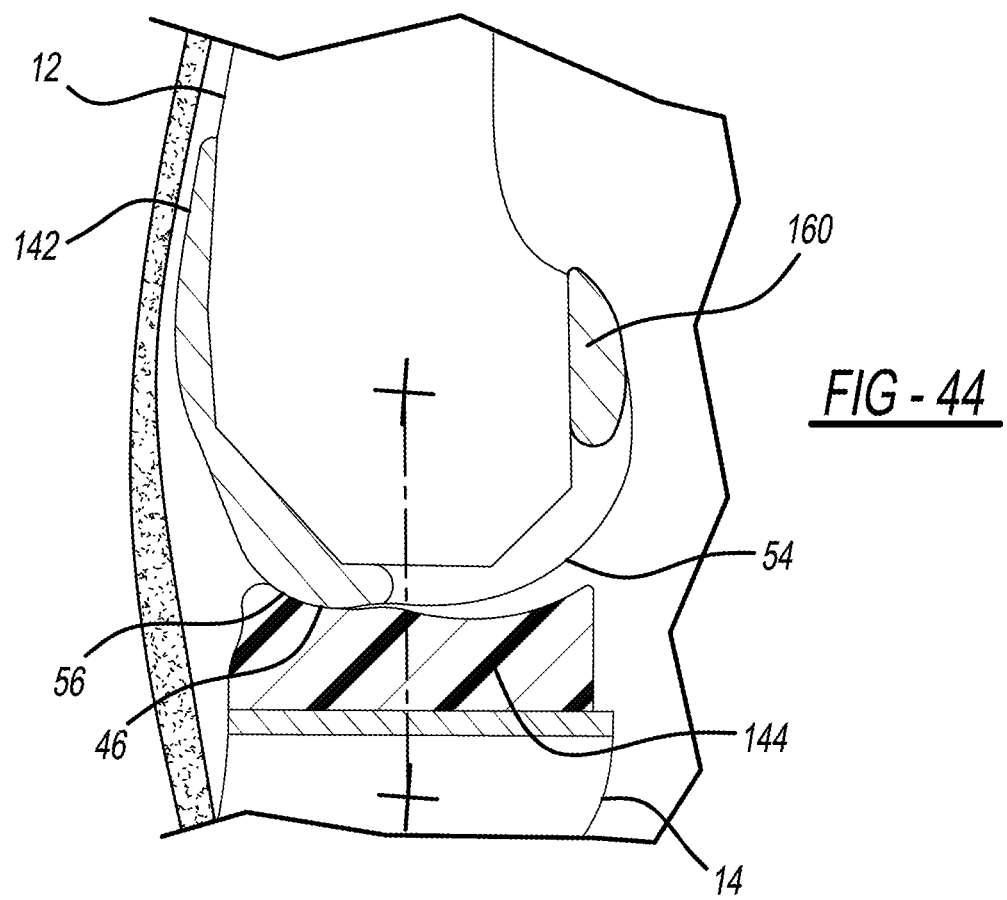
Figure 45:
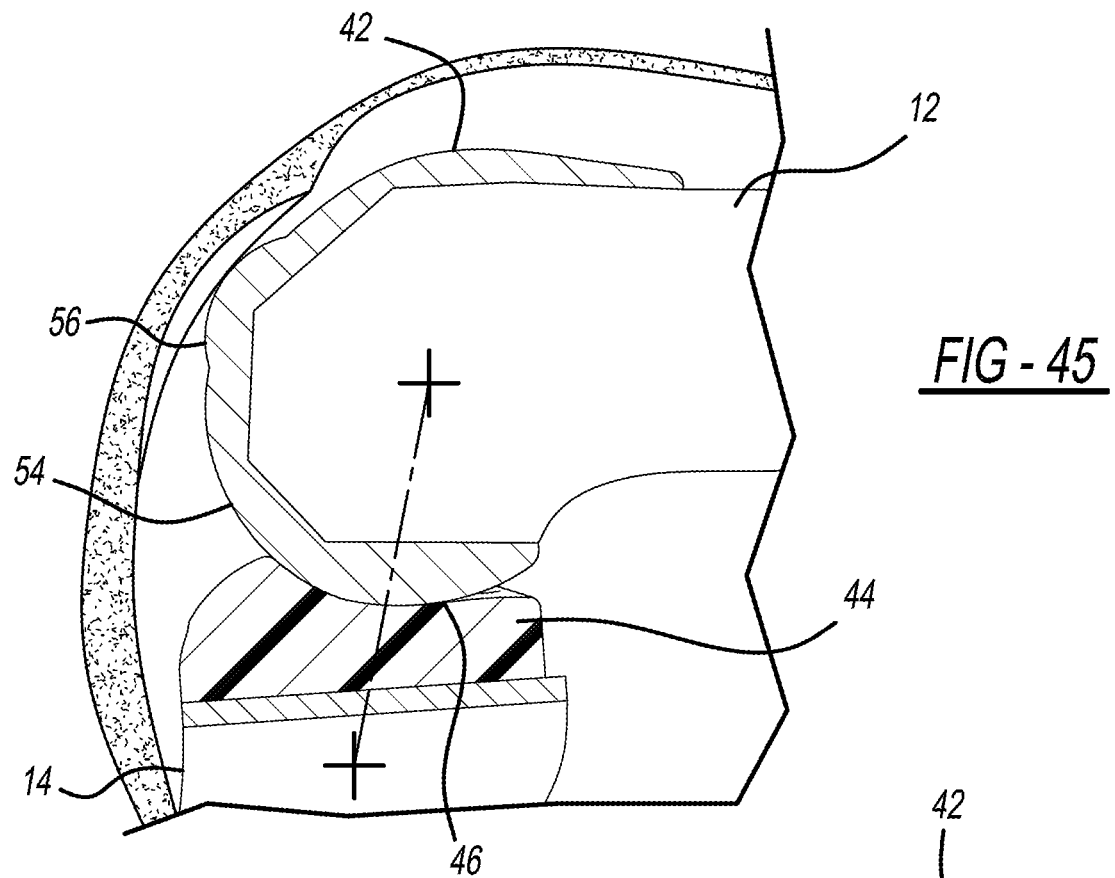
Figure 46:
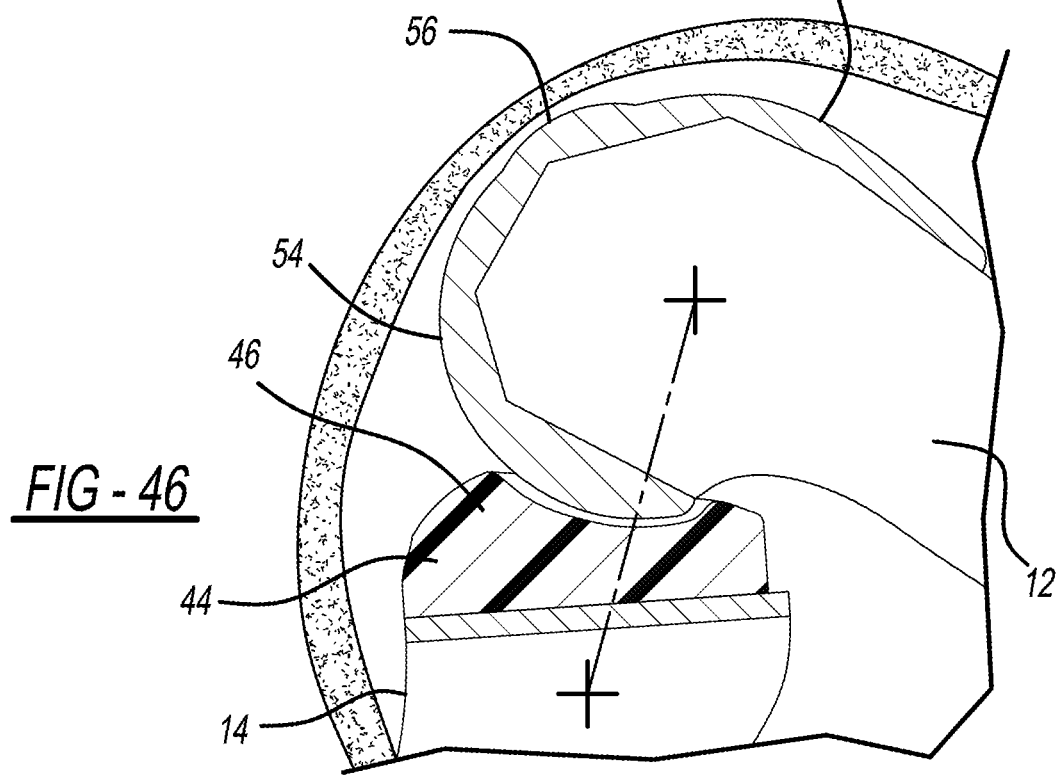
Figure 47:
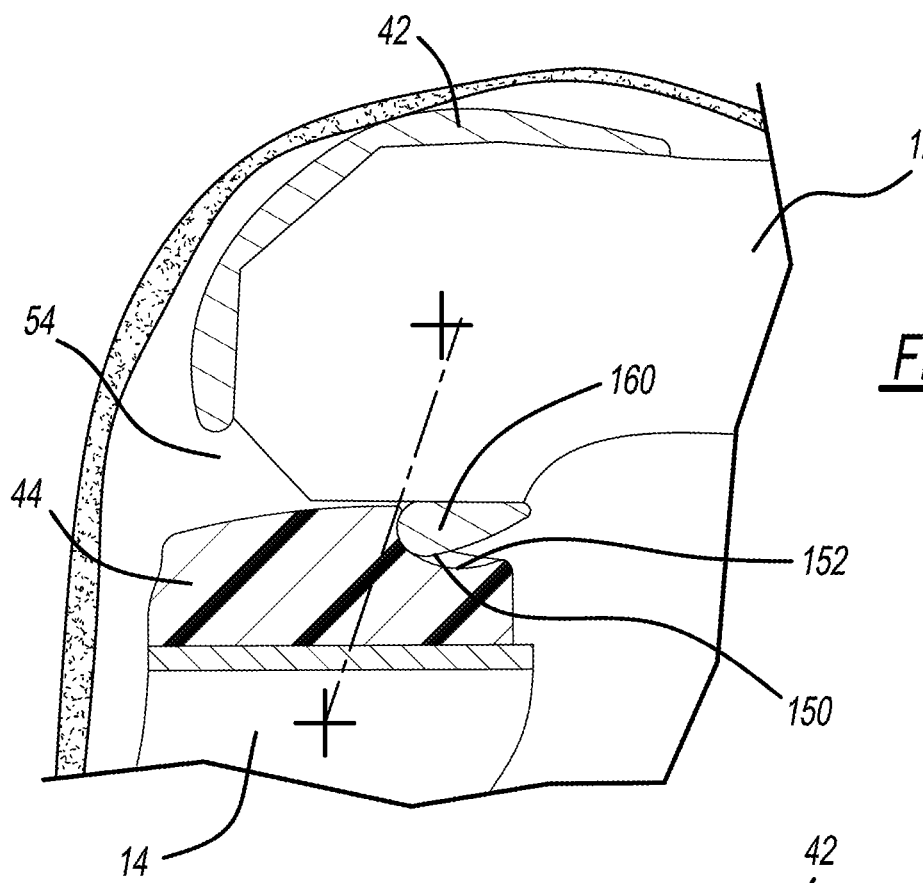
Figure 48:
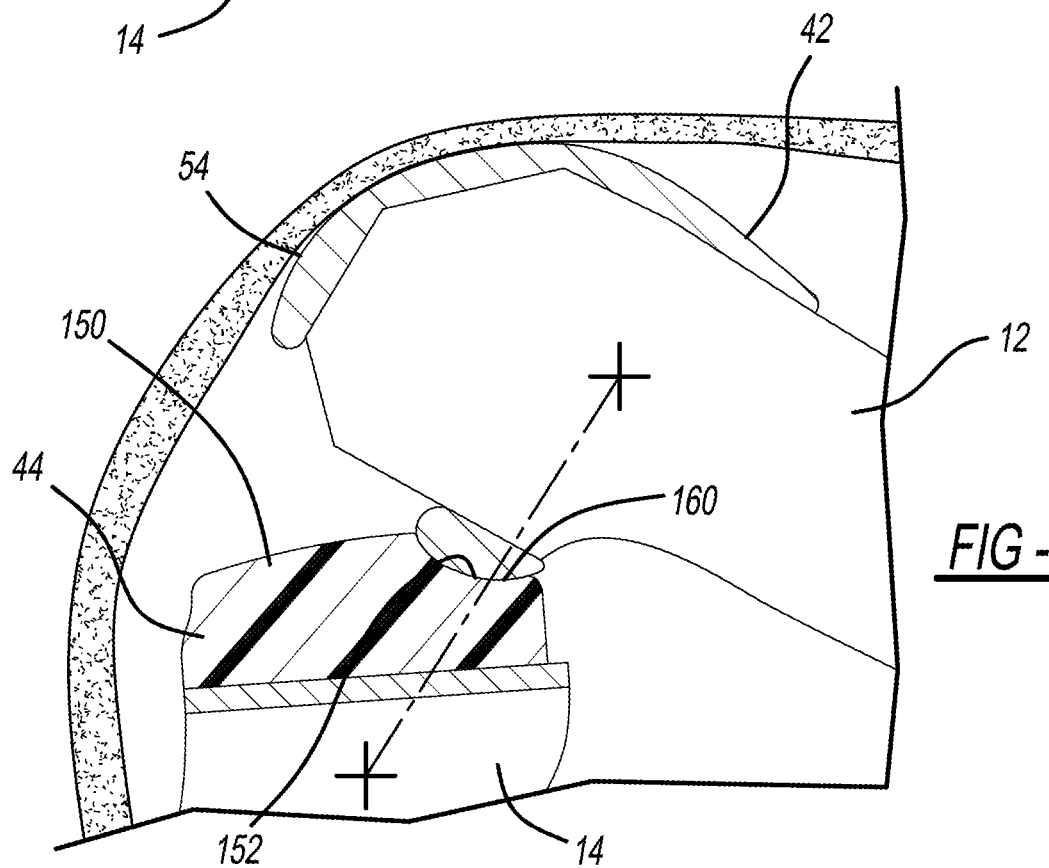

FIGS. 29-48 illustrate a total knee replacement prosthetic implant in accordance with a second embodiment of the present invention in which FIG. 29 is a pictorial view of total knee replacement prosthetic implant particularly showing the interface surfaces between the femur and tibia components;

FIG. 30 is a top view of the tibia component shown in FIG. 29;

FIG. 31 is a cross-sectional view taken along line 31-31 from FIG. 30;

FIG. 32 is a cross-sectional view taken along line 32-32 from FIG. 30;

FIG. 33 is a cross-sectional view taken along line 33-33 from FIG. 30;

FIG. 34 is a cross-sectional view taken along line 34-34 from FIG. 30;

FIG. 35 is a cross-sectional view taken along line 35-35 from FIG. 30;

FIG. 36 pictorial view of the tibia component;

FIG. 37 is a pictorial view of the femur and tibia components of the present invention shown in a conforming position;

FIG. 38 is a pictorial view of the femur implant component;

FIG. 39 is a side view of the femur component;

FIG. 40 is a cross-sectional view taken along line 40-40 from FIG. 38;

FIG. 41 is a cross-sectional view taken along line 41-41 from FIG. 38;

FIG. 42 is a cross-sectional view taken along line 42-42 from FIG. 38;

FIG. 43 is a cross-sectional view taken along line 43-43 from FIG. 38;

FIG. 44 is a cross-sectional view through the implanted components showing the medial interface at full extension;

FIG. 45 is a sagittal section through the medial interface of the implant components showing the joint at mid flexion;

FIG. 46 a sagittal section through the medial interface of the implant components shown in the joint at full flexion;

FIG. 47 is a sagittal section through the medial interface of the implant components showing the joint at mid flexion taken on the plane of section 41-41; and FIG. 48 a sagittal section through the medial interface of the implant components shown in the joint at full flexion taken on the plane of section 41-41.

Third Embodiment

Figure 49:
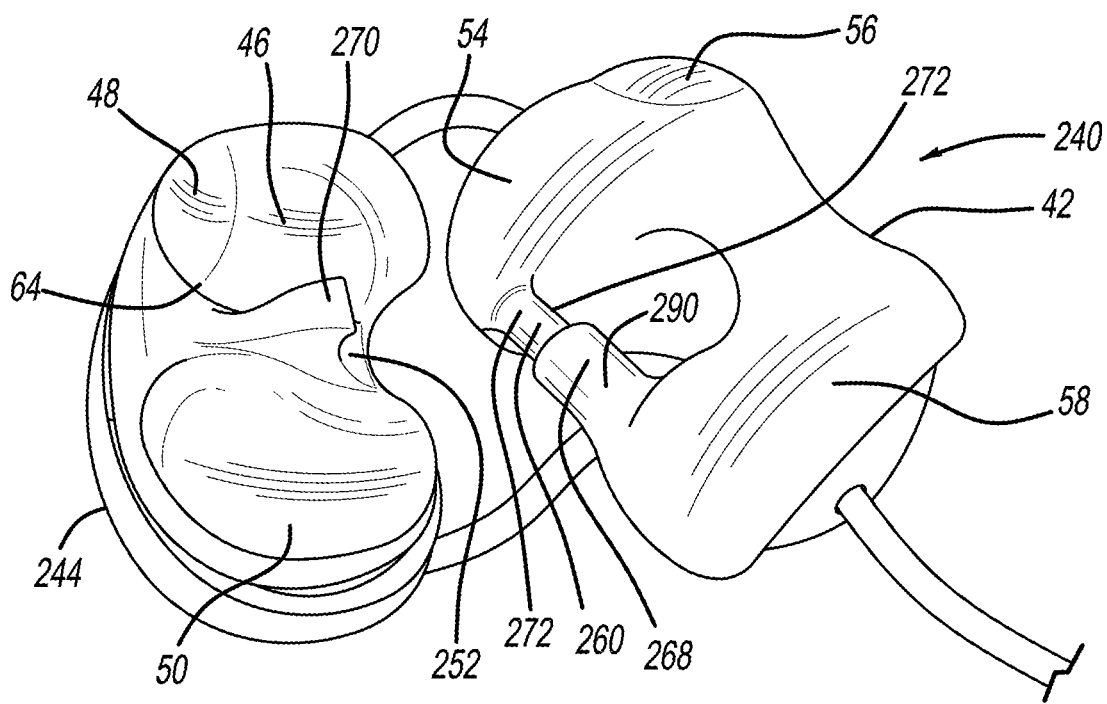
Figure 50:
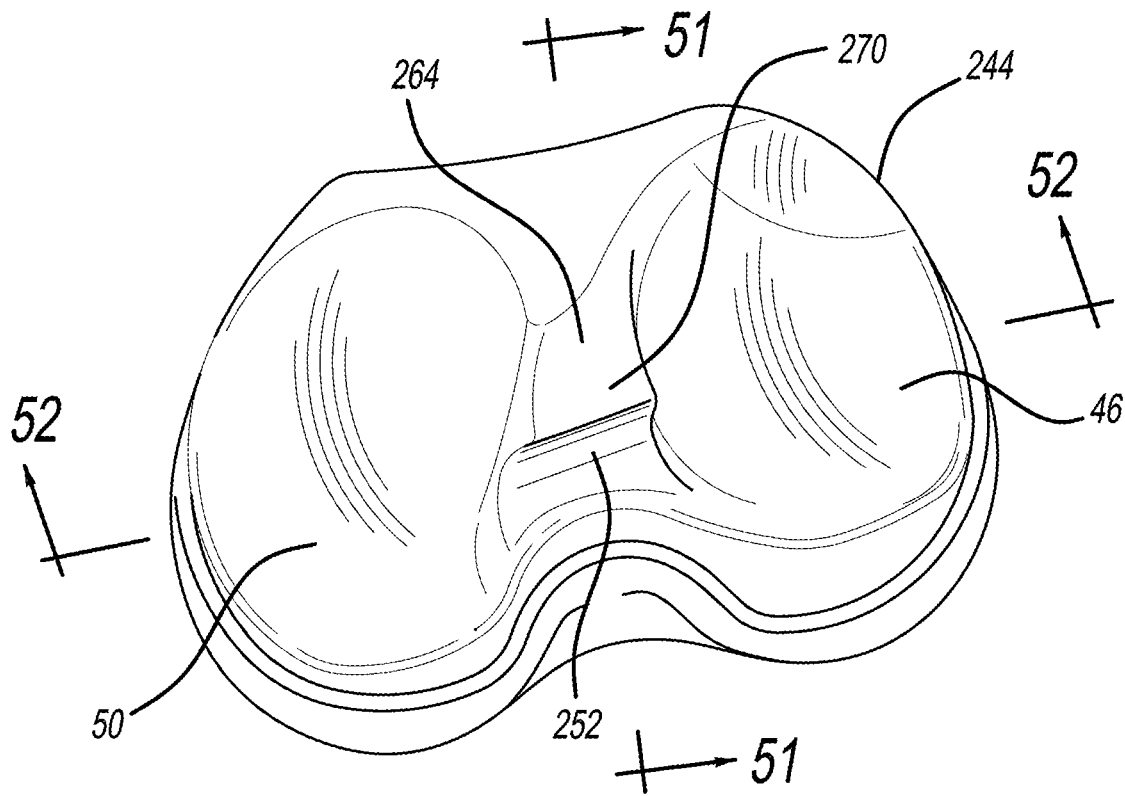
Figure 51:
Figure 52:
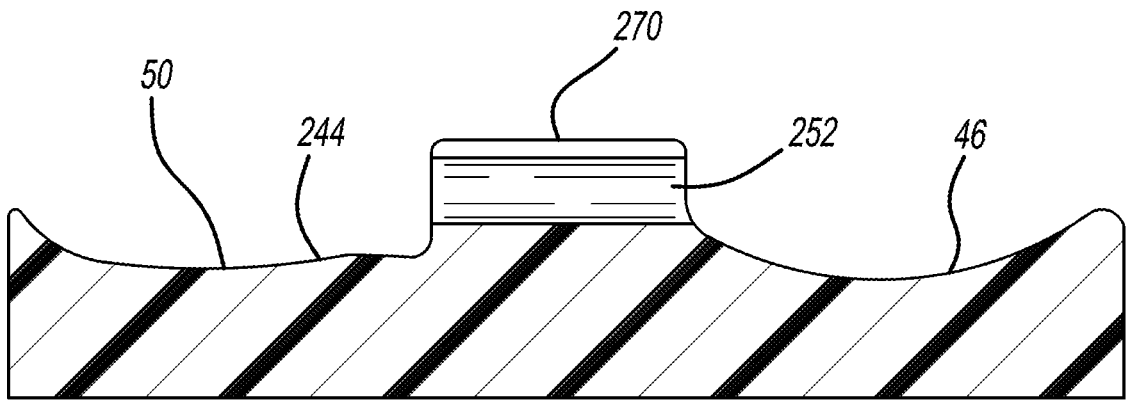
Figure 57:
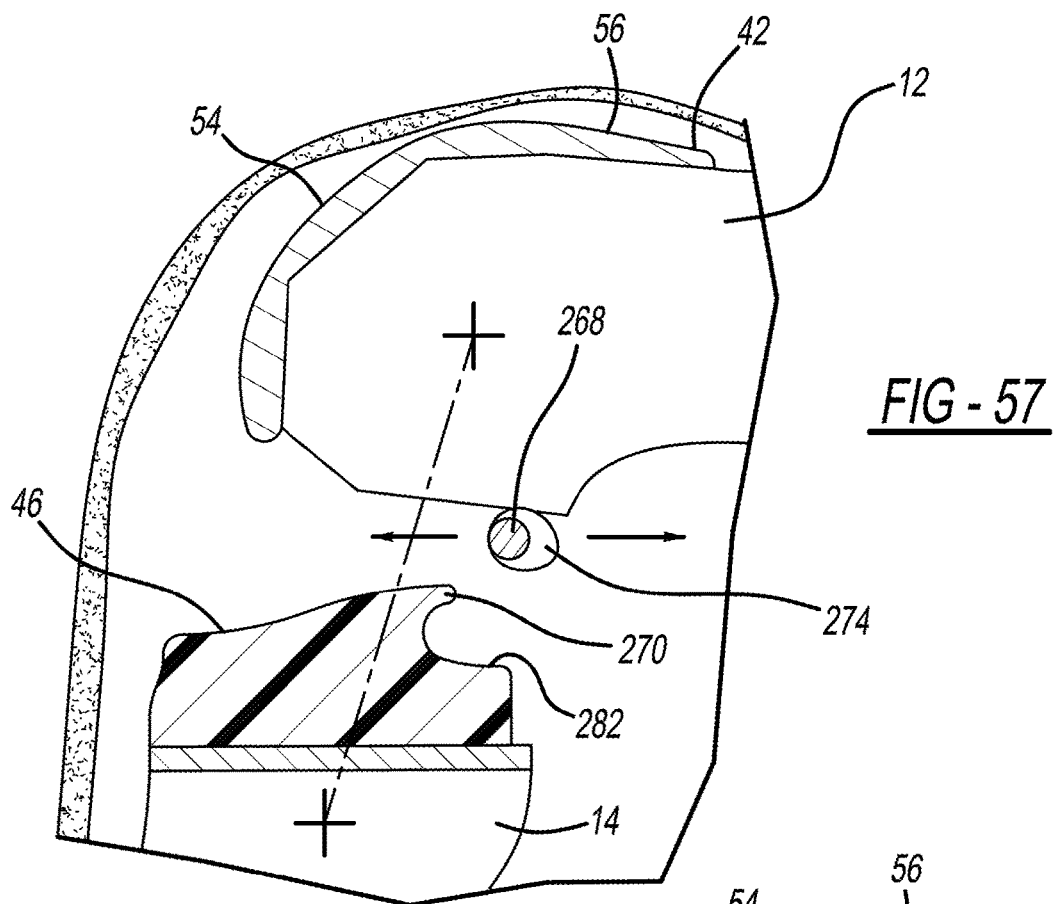
Figure 58:
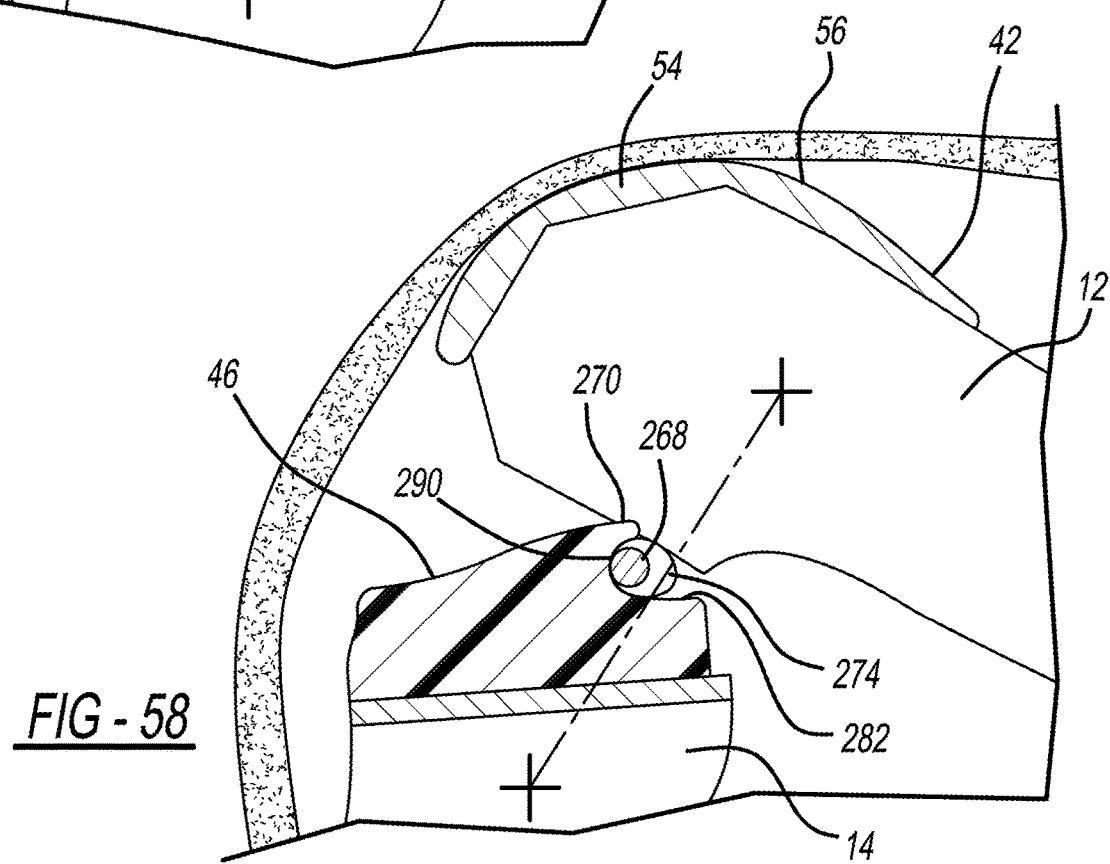
Figure 59:
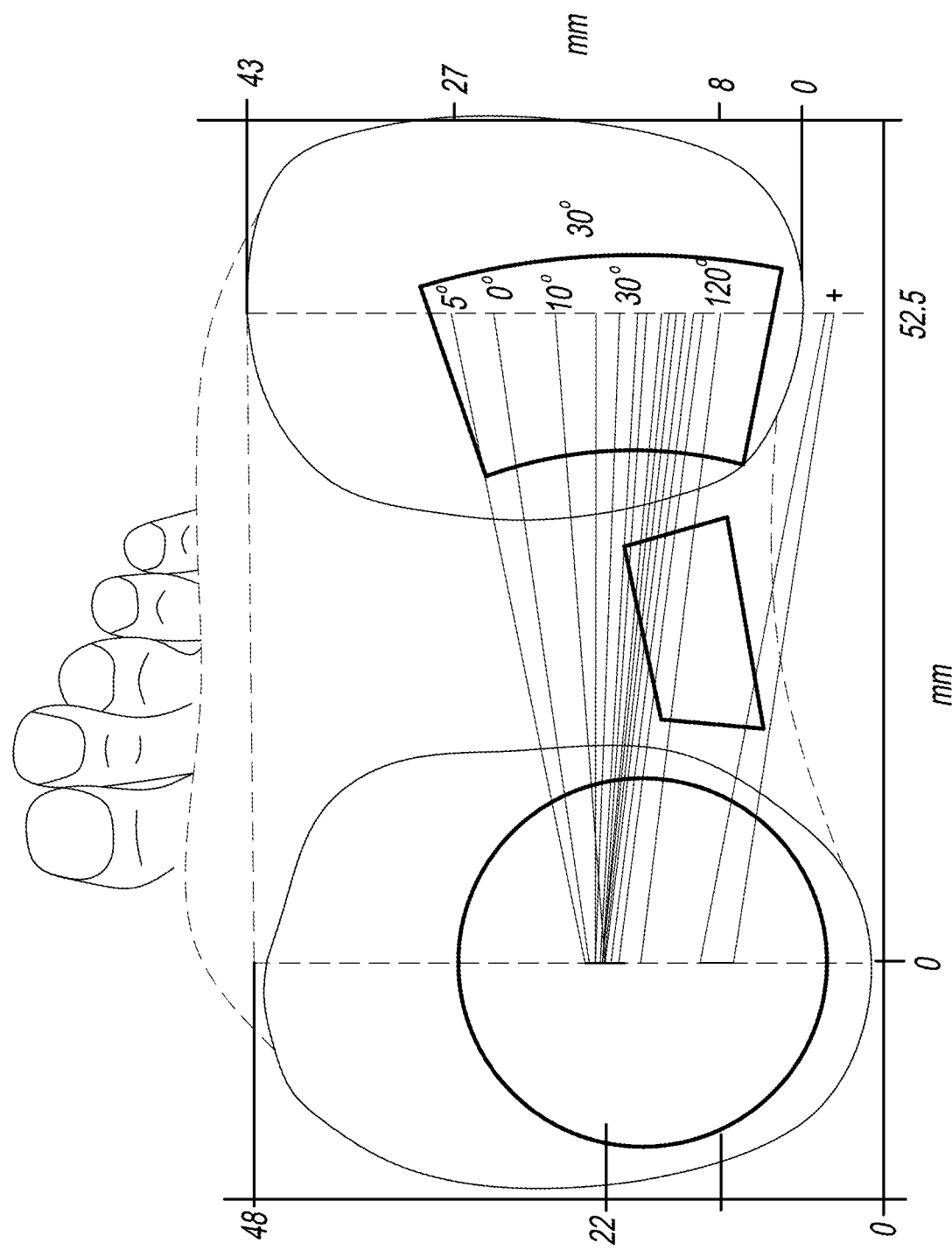

FIGS. 49-59 illustrate a total knee replacement prosthetic implant in accordance with a second embodiment of the present invention in which FIG. 49 is a pictorial view of total knee replacement prosthetic implant particularly showing the interface surfaces between the femur and tibia components;

FIG. 50 is a top view of the tibia component shown in FIG. 49;

FIG. 51 is a cross-sectional view taken along line 51-51 from FIG. 50;

FIG. 52 is a cross-sectional view taken along line 52-52 from FIG. 50;

FIG. 53 is a is a pictorial view of the femur implant component;

FIG. 54 is a cross-sectional view taken along line 54-54 from FIG. 53;

FIG. 55 is a cross-sectional view taken along line 55-55 from FIG. 53;

FIG. 56 is a cross-sectional view taken along line 56-56 from FIG. 53;

FIG. 57 is a sagittal section through the medial interface of the implant components showing the joint at mid flexion;

FIG. 58 is a sagittal section through the medial compartment of the implant components shown in the joint at full flexion; and FIG. 59 is a diagram of the tibia plateau overlaid with solid lines each representing an imaginary axis of rotation connecting the centers of the medial and lateral femoral flexion facets over a range of joint articulation.

DETAILED DESCRIPTION OF INVENTION

FIGS. 1 and 2 illustrate a human leg showing the limb outline and bone features of the upper and lower leg 10.

Primary bones are femur 12 in the upper leg and tibia 14 in the lower leg (the fibula is not shown). Femur 12 forms head 18, femur shaft 20, and a pair of laterally disposed condyles; namely, medial condyle 22 and lateral condyle 24 separated by the intercondylar fossa 26. In this view the patella is not shown but would overlie the intercondylar fossa 26. Condyles of tibia 14 form articulating joint interface surfaces including medial tibia plateau 28 and lateral tibia plateau 30. Menisci are present between the joint interface surfaces (not illustrated). In FIG. 1 the fibula is not illustrated as it does not play a direct role in a description of this invention.

Figure 3:
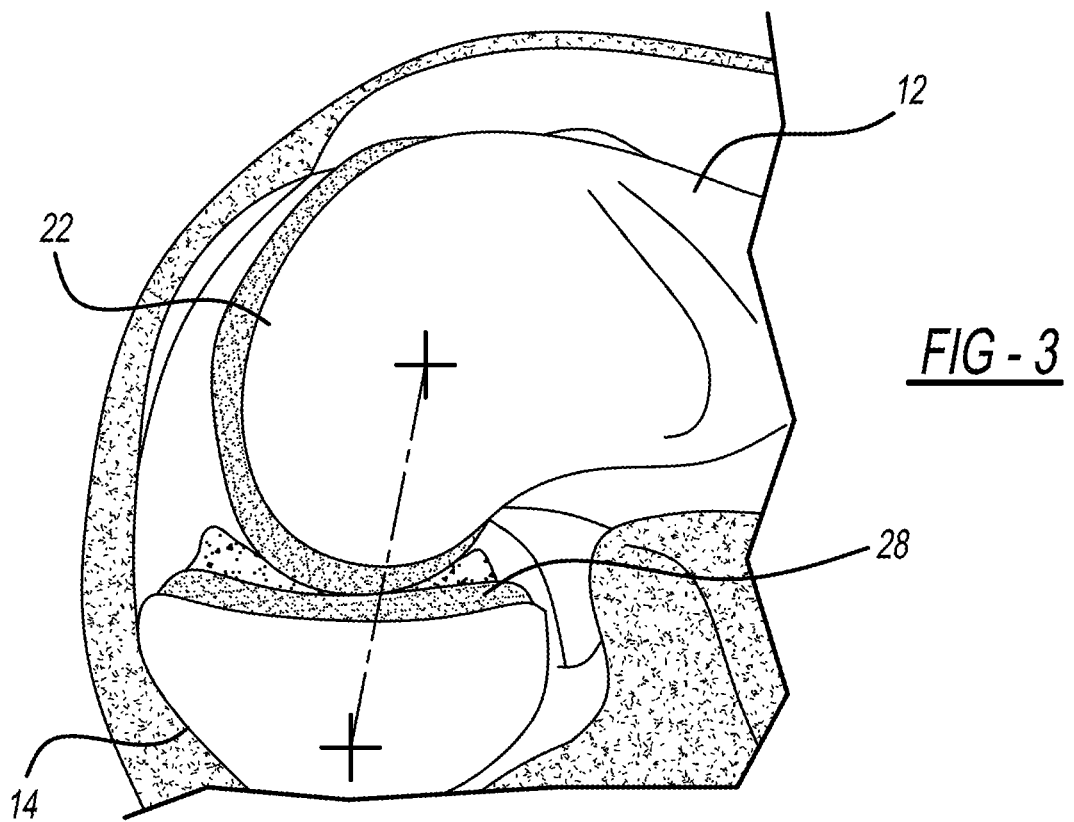
FIG. 3 is a sagittal section through the human knee at mid flexion showing particularly the medial interfaces.
Figure 4:
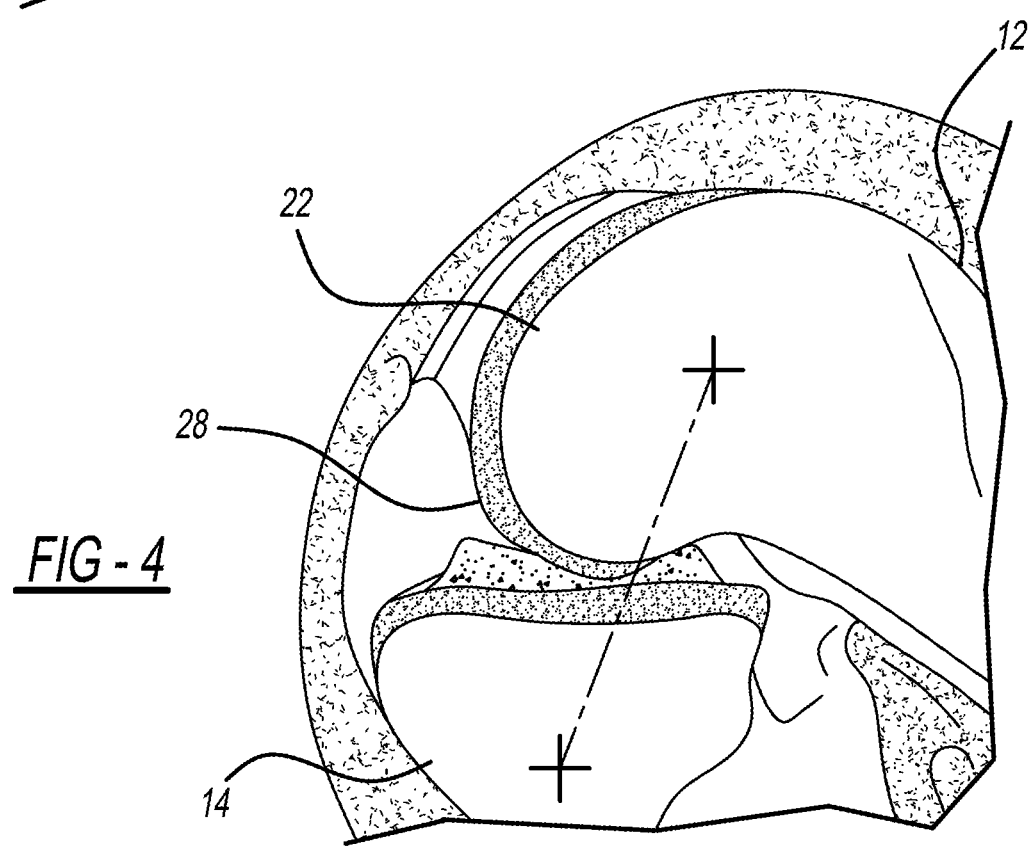
FIG. 4 is a sagittal section through the human knee at full flexion showing particularly the medial interfaces.
Figure 5:
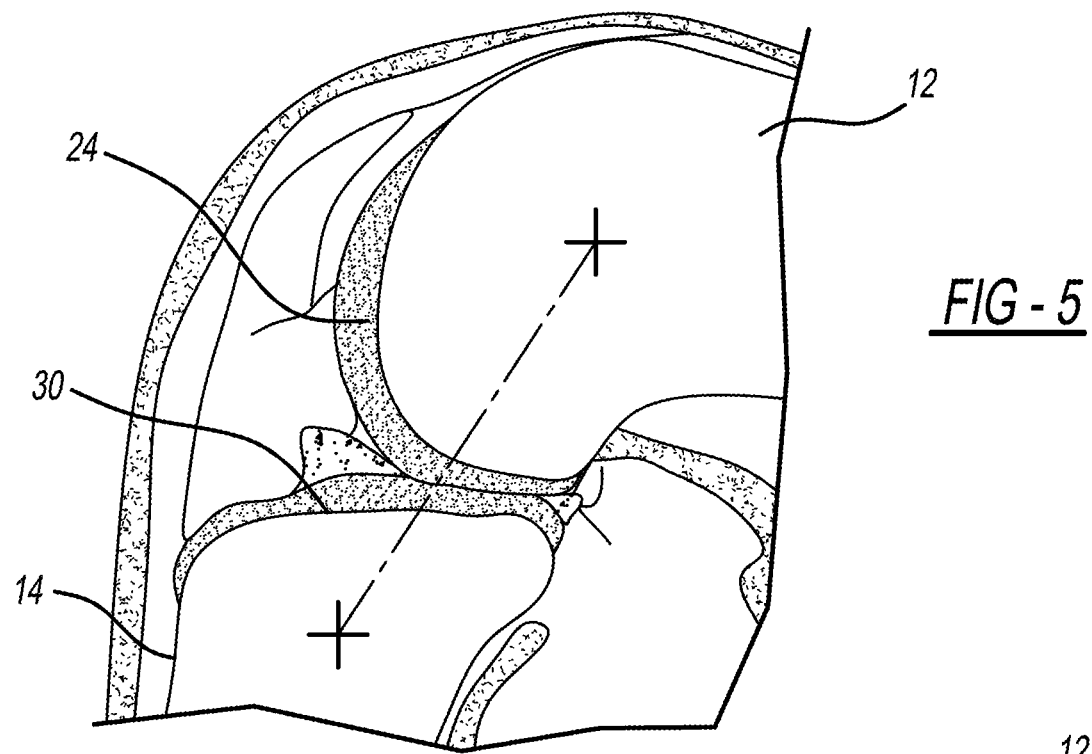
FIG. 5 is a sagittal section through the human knee at mid flexion particularly showing the lateral interfaces.
Figure 6:
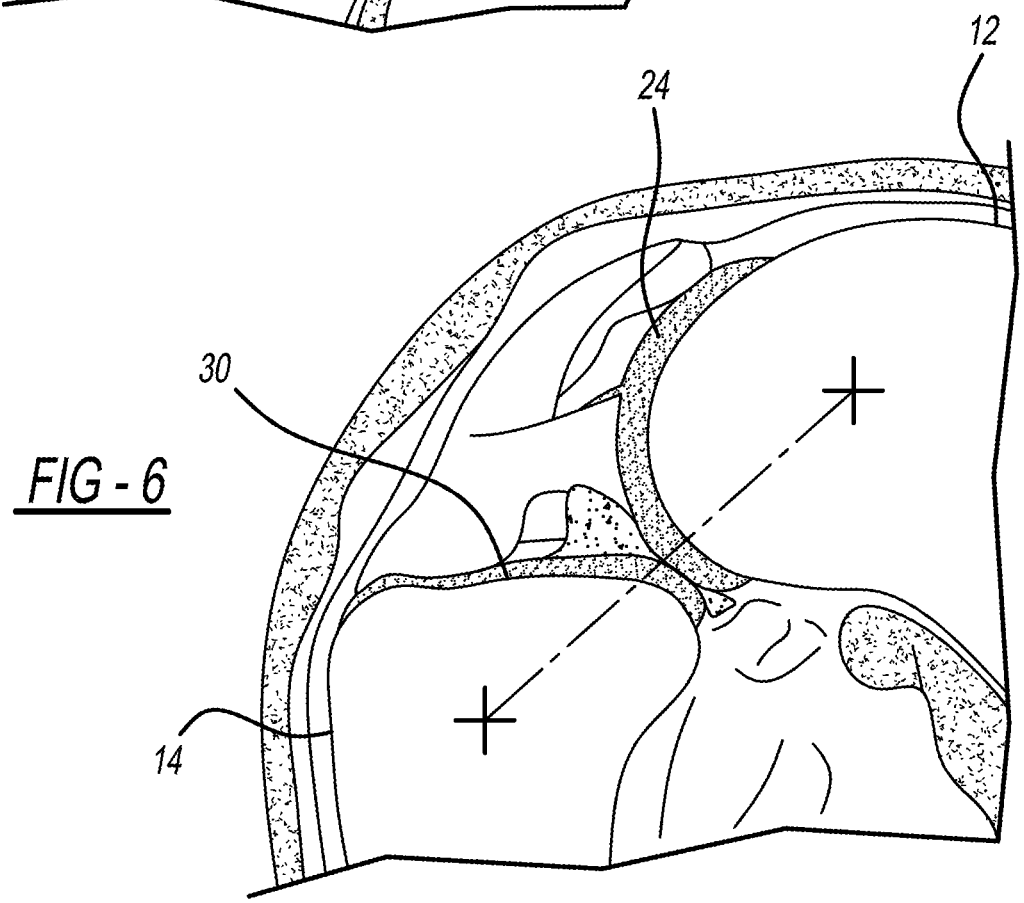
FIG. 6 is a sagittal section through the human knee at full flexion particularly showing the lateral interfaces.

As a means of explaining features of the present knee prosthetic implant, additional features and behavior of a typical living knee are further described. FIG. 3 illustrates the flexion condition of the medial condyle joint interface. FIG. 3 represents flexion of about 90 degrees or mid flexion, whereas FIG. 4 illustrates full flexion of about 120 degrees. In the Figures reference marks are shown as crosses for the femur and tibia with a broken line drawn joining them. These broken lines can be thought of as approximating a line of tension of the respective medial and lateral collateral ligaments or a line through the center of pressure or center of contact between the joint interfaces. It should be noted that in FIGS. 3 and 4, the broken lines do not move significantly at the medial interface in the anterior-posterior direction at this range of flexion. In fact, the medial joint interface acts essentially as a ball-in-socket type joint in which the femoral medial condyle 22 forms a generally convex hemispherical surface which interfaces with a corresponding concave hemispherical surface formed in the medial tibia plateau 28. FIGS. 5 and 6 illustrate flexion states at the lateral condylar interface. FIG. 5 represents mid flexion of about 90 degrees, whereas FIG. 6 represents full flexion at about 120 degrees. It is noted that the femoral lateral condyle 24 is essentially displaced posteriorly off the surface of the lateral tibia plateau 30 in this condition (referred to later as a "roll-off" behavior). This would appear to produce an unstable condition; however, medial and cruciate ligaments provide stability in the normal healthy knee despite the separation of conforming surfaces at the lateral side.

Figure 6A:
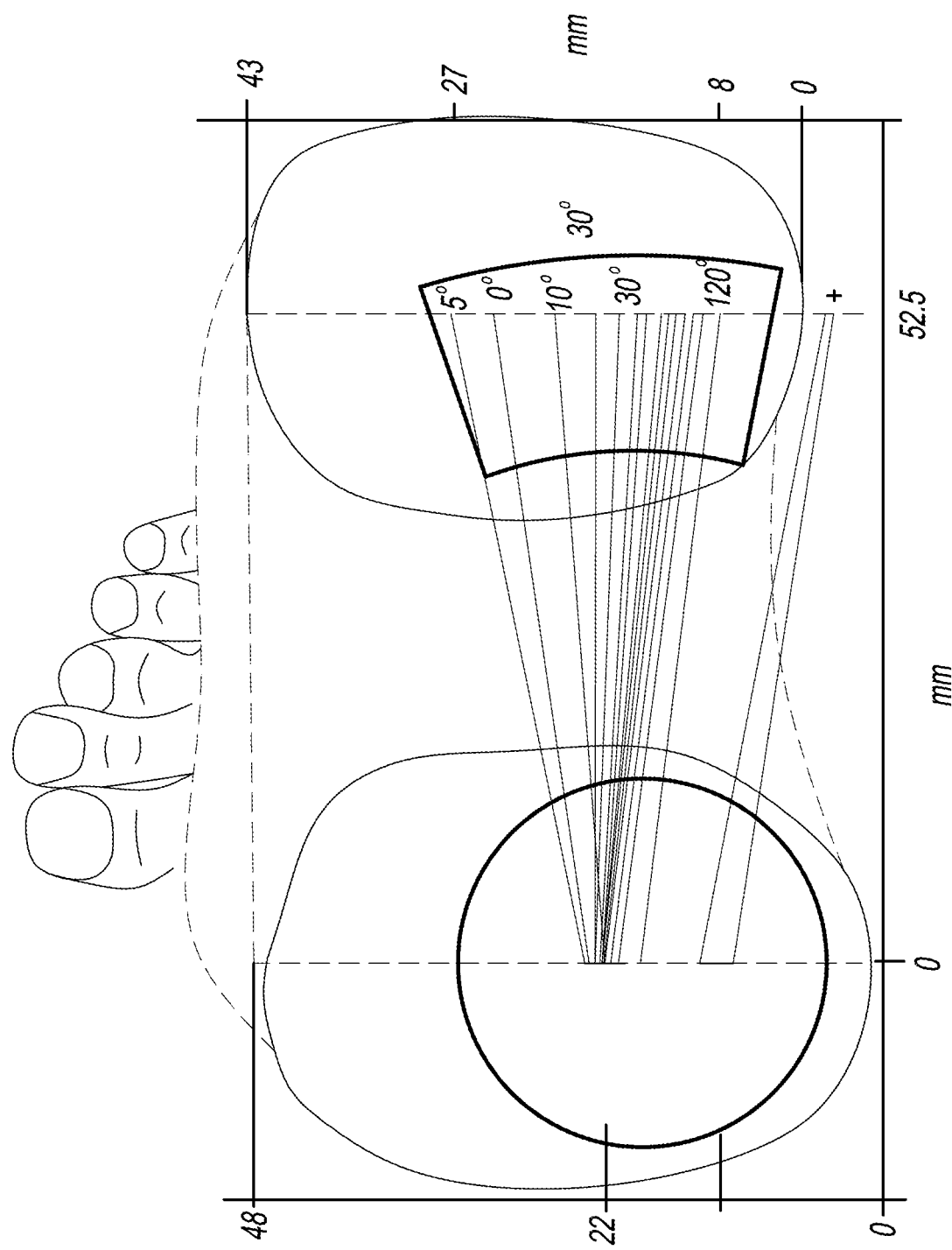
FIG. 6A is a diagram of the tibia plateau overlaid with solid lines each representing an imaginary axis of rotation connecting the centers of the medial and lateral femoral flexion facets over a range of joint articulation.

FIG. 6A represents centers of contact at the condyle of the human knee illustrating the instantaneous axes of rotation at various articulation conditions. Lines shown in the diagram designate imaginary axes of rotation at various states of knee flexion. As evident, the center of contact at the medial side moves little in the range of flexion illustrated in the figure. At the lateral side however, significant anterior-posterior position changes occur during flexion, thus the interface can be thought of as rolling contact at the interface although the interaction is more accurately described as a combination of rolling and sliding motion. This movement in the lateral interface position during full flexion results in internal rotation of the tibia upon.

First Embodiment

The prior Figures and above description refer to structures of a healthy living human knee. In accordance with the first embodiment of the present invention, a knee prosthetic implant 40 shown in the FIGS. 7-28 is provided incorporating femur component 42 and tibia component 44. The second embodiment of the present invention is illustrated in FIGS. 29-48. The third embodiment of the present invention is illustrated in FIGS. 49-59. Components 42 and 44 are intended to be affixed after certain bony structures of the diseased knee are surgically removed. Fixation of components 42 and 44 may be done by conventional surgical techniques including use of bone cements, surgical fasteners, and transplanted marrow.

Knee prosthesis 40 uniquely provides for knee joint stability in three distinct states of flexion as they are identified in this description; namely, full extension to minor hyper extension −5° to 10° ("full extension"), normal or mid flexion range 10° to 115° ("mid flexion"), and full flexion beyond about 115° ("full flexion"). These three states of articulated condition represent different kinematic and stability considerations which are accommodated by particular interface facets of implant 40.

With reference to the Figures, prominent features of femur component 42 and tibia component 44 are shown. Particular reference is made to features of the various surfaces or facets. FIG. 7 illustrates tibia component 44 as forming a first medial concave surface 46, second medial concave surface 48, first lateral concave surface 50, and second lateral concave surface 52. Femur component 42 forms first medial convex surface 54, second medial convex surface 56, first lateral convex surface 58, and second lateral convex surface 60.

FIGS. 9 through 13 will provide cross-sectional views through tibia component 44 and serve to further describe the configuration of the concave surfaces which it forms. FIG. 9 shows first lateral surface 50 as concave in shape with a lesser radius of curvature as compared with first medial surface 46. Second lateral surface 52 has a concave surface and is much smaller in plan view area as compared with surface 50. Surfaces 50 and 52 join at interface rim 62. The lateral and medial surfaces are separated by central ridge 64. FIG. 10 is an anterior-posterior section through first lateral surface 50 showing its generally concave shape. FIG. 11 shows the curvature of surface 46. FIG. 12 is an anterior-posterior section through medial surfaces 46 and 48; both are concave in shape and at their interface form rim 66. FIG. 13 is an anterior-posterior section through first and second lateral surfaces 50 and 52 showing the junction between these two surfaces and rim 62.

Referring particularly to FIGS. 7, and 15-23, femur component 42 forms convex surfaces which interact with the previously described tibia component concave surfaces. First referring to the medial side, first and second convex surfaces 54 and 56 are formed which are characterized as generally hemispherical in shape. Convex surfaces 54 and 56 have radii which approximately match their corresponding engaging tibia concave surfaces 46 and 48, respectively. The lateral side forms first lateral surface 58 which is generally shaped as a partial curved cylinder. Second lateral convex surface 60 is formed by a medially displaced protuberance much smaller in plan view area than surface 58.

FIG. 16 indicates numerous cross-sections through the femoral component 42. The cross-sectional views 18-22 provide further definition of the shapes of the previously described convex surfaces. FIG. 18 illustrates the relative position of second medial convex surface along the arc formed by first surface 54. FIG. 20 particularly illustrates second lateral surface which forms a protuberance at the distal end of the arc formed by surface 58.

FIG. 24 provides a cross-section through the medial joint interfaces at a state of full extension. In this position, second medial surface 56 which as described previously is a relatively small radius protuberance engages with second medial surface 48 to cause a slight vertical separation of the joint at the medial side. In this condition kinematic behavior of a living knee is characterized by some "lifting off" displacement at the medial side as the lateral interface undergoes the rocking motion (i.e. the bones separated at the lateral side). At this articulated condition, the position of the joint centers illustrated separate from one another which corresponds with a tightening of the healthy medial collateral ligament. Thus the medial interface does not act entirely as the idealized spherical bearing configuration (desirably maintained in many prior art TKA procedures). This tightening of the medial collateral ligament occurs at a condition of the joint in which a high degree of static and dynamic stability is necessary, without requiring the same continuous tension in these ligaments in other conditions of articulation. In full flexion, the lateral interface behaves in a manner similar to that described previously for normal flexion range, undergoing the rocking or sliding contact motion discussed but without significant enlargement of the conforming surface separation.

The surfaces of the prosthetic implant 40 act to provide joint stability during normal flexion from full extension is described next with particular reference to FIGS. 25-28. In this condition, on the medial side, tibia surface 46 is in contact with femur surface 54. Femur surface 54 is characterized as a generally hemispherical surface. The conforming first medial tibia surface 46 is likewise formed of a concave hemispherical surface. As mentioned previously, in the normal knee this medial interaction is generally characterized as a ball-in-socket arrangement, with little change in the center of rotation of the femur relative to the tibia during this range of flexion (see FIG. 6A). The interaction at the medial side provides a high degree of anterior-posterior restraint. This interaction is further illustrated with reference to FIG. 14 in which an imaginary sphere is placed on surface 46. On the lateral side however, anterior-posterior displacement of the interface is enabled. Here first lateral tibia surface 50 interfaces with first femur surface 58. Surface 50 can be described as the shape of a hemisphere dragged along a curved path to provide the translation characteristic mentioned previously, and which is illustrated by the arrow in FIG. 14. Likewise, first medial femur surface 54 is formed as a hemisphere but spins along the previously noted curved path during flexion. The shapes of the interfacing surfaces in this condition do not need to conform to idealized solid geometric shapes such as hemispheres etc. As described however, the medial side undergoes little anterior-posterior displacement during flexion whereas the lateral side allows the interior-posterior displacement characteristic mentioned previously. The shapes of these interfacing surfaces of the implant are made to provide for this interaction. It is also noted that component interaction is referred to as at a point of interface whereas, due to compressibility and mechanical compliance of the interfacing elements, the interaction can be better described as an area of pressure defining a center of pressure related to the idealize points of contact mentioned previously.

A state of full flexion of the implant 40 is described. As mentioned previously in the normal knee and as described by FIG. 6, a roll-off of the interfacing femur and tibia surfaces occurs at the lateral interfaces in the normal knee. In the healthy knee, stability is provided through other additional supporting structures including but not limited to cruciate ligaments. In order to provide stability in this condition, the prosthetic joint implant 40 in accordance with this invention, such flexion is accompanied by engagement between tibia lateral surfaces 52 and 60. Contact at the medial side is maintained through interaction of surfaces 54 and 46. This interaction is best illustrated with reference to FIG. 28. Stability in this case is provided through conformal interaction between the prosthetic implant surfaces, as opposed to contributions from cruciate ligament structures as described previously. Thus knee prosthesis 40 in accordance with this first embodiment of the invention does not permit the separation of interfaces at the lateral side to occur at full flexion. Contact at the lateral side simultaneously transitions from contact between surfaces 50 and 58, to surfaces 52 and 60. FIG. 27 shown in mid flexion shows a condition where surfaces 50 and 58 are engaged. However, when moving to full flexion shown in FIG. 28, the interface moves back to interaction between surfaces 60 and 52. This provides the mechanical support and the desired inward rotation of the tibia exhibited in the healthy knee at full flexion.

Stability is provided by prosthetic 40 in each range of flexion by two separated areas of contact between tibia component 44 and femoral component 42; one at the medial interface and another at the lateral interface. The lateral separation of these contact areas provides lateral stability and integrity of the relationship of the knee components.

Second Embodiment

FIGS. 29-48 illustrate knee prosthesis 140 in accordance with a second embodiment of the present invention. Elements of the second embodiment which are identical to those of the first embodiment are identified by like reference numbers; whereas elements which differ between the embodiments that have related function are identified in the second embodiment with 100 added to their reference numbers (e.g. prosthesis 40 and 140). FIGS. 29-48 of the second embodiment correspond with FIGS. 7-28 of the first embodiment in the same order (however FIGS. 47 and 48 show the medial interface unlike FIGS. 27 and 28). Reference is made to the above presented description of elements of the second embodiment having the same reference numbers as the first embodiment.

The second embodiment of knee prosthesis 140 differs from the first embodiment in the positioning of surfaces 52 and 60, or in this instance 152 and 160. Rather than surfaces 60 and 52 presented at the lateral interface, their function is served by surfaces positioned at the lateral edge of the medial interface (these surfaces may be referred to in this embodiment as third medial surfaces). The position of surface 152 is evident in the cross-sectional view FIG. 31. For this embodiment, the lateral tibia component concave surface 50 is smooth and continuous. FIGS. 38 and 39 and the related cross-sectional views FIGS. 40-43 provide further definition regarding the surface configurations. FIG. 44 shows the medial interface at full extension exhibiting the liftoff behavior as described in connection with FIG. 24. FIGS. 45 and 46 show an identical behavior at an edge of the medial interface as previously shown in FIGS. 25 and 26. These sections are taken at near the medial edge of the medial interface. FIGS. 47 and 48 are also cross-sections through the medial side but along a plane near the lateral edge of the medial interface and show the interaction at mid and full flexion. FIG. 47 shows that at mid flexion, surfaces 160 and 150 have not yet engaged. FIG. 48 shows the engagement between surfaces 152 and 160. This interaction provides for internal rotation of the lower leg during flexion. At this position of flexion, conformal contact at the medial interface occurs in two areas, one at the medial edge as shown in FIG. 46, and one at the lateral edge shown in FIG. 48.

In this embodiment of prosthesis 140 a separation or rolling on-off behavior at the lateral interfaces is permitted to occur with stability being provided by a pair of medial interfaces as described previously. Like prosthesis 40, prosthesis 140 provides two areas of contact throughout the full range of knee motion.

Third Embodiment

FIGS. 49-59 illustrate knee prosthesis 240 in accordance with a third embodiment of the present invention. Elements of the third embodiment which are identical to those of the first and second embodiment are identified by like reference numbers; whereas elements which differ from the first embodiment that have related function are identified in the third embodiment with 200 added to their reference numbers (e.g. prosthesis 40 and 140). FIGS. 49-59 of the third embodiment correspond to a variety of figures of the first embodiment. Reference is made to the above presented description of elements of the third embodiment having the same reference numbers as the first embodiment.

The third embodiment of knee prosthesis 240 differs from the first embodiment in how surfaces 252 and 260 are provided. Unlike in the first embodiment, in which second lateral surface 52 is a depression on the same face on tibia component 244 as first lateral surface 50, in the third embodiment a concave projection surface 252 is provided projection 270, which lies between the first lateral surface 50 and first medial concave surface 46. Projection 270 is a generally hook- or latch-shaped element which is a prominence on the face of the tibia component 244, with concave projection surface 252 being positioned such that contact with a portion of the femur component 242 is facilitated. As can be most clearly seen in FIG. 50, a surface of projection 270 acts as a central ridge 264, which separates the lateral side of the tibia component 244 from the medial side.

Femur component 242 includes a second lateral convex surface 290, which is presented on central shaft 260. Shaft 260 includes two substantially cylindrical elements: medial element 272, and lateral element 268. Shaft 260 lies between the first medial convex surface 54 and first convex surface 258. As depicted in the embodiment of FIG. 49, the medial element 272 has a smaller diameter and thinner profile than does lateral element 268. Formed off of the shaft 260 and projecting toward the interior of the femur component 242 is extension 274. As can best be seen in FIGS. 55 and 56, in this embodiment the lateral element 268 and the medial element 272 of shaft 260 may not be concentric with one another. The eccentricity of these shaft components can be seen by the positions of longitudinal axes 284 and 286 in FIG. 56. The eccentric arrangement allows the shaft 260 to act similarly to a camshaft during bending.

As in other embodiments, medial convex surface 54 of femur component 242 can be seated in first medial concave surface 46 of tibia component 244, and lateral convex portion 258 can likewise be seated in first lateral concave surface 50.

As the knee bends from mid flexion (about 90 degrees) to full flexion (about 120 degrees), the convex surface of lateral element 268 rotates until it contacts concave projection surface 252 of the tibia component 244. The radius of curvature of concave projection surface 252 is somewhat larger than that of lateral element 268 such that the lateral element 268 is readily accommodated within the hook structure of projection 270. When the knee is bent to an angle of about ninety degrees, the lateral element 268 remains slightly above the plane in which projection 270 resides (see FIG. 57). In this arrangement, the femur component 242 is able to slide forward and backward relative to the tibia component 244 above posterior surface 282.

As the knee continues to bend to the full flexion condition (110 degrees, as shown in FIG. 58), there is contact between lateral element 268 of shaft 260 and concave projection surface 252. Such a configuration provides for securing the halves of the device 210 in the anterior direction, while allowing freedom of motion in the vertical direction for when the knee is in the full flexion condition (when the lateral portions disengage from one another.) The smaller diameter of lateral element 272 allows for a degree of lateral movement of the femur component 242 while engaged with tibia component 244 during more extreme flexion. As can be seen in FIG. 58, the hinge-like arrangement of the central shaft 260 within projection 270 allows for contact between these two components throughout the range of more extensive bending, even when other portions of the prosthesis are disengaged from one another.

In all embodiments of the knee prosthetics 40, 140, and 240, stability in all phases of flexion; full extension, mid flexion, and full flexion is provided by maintaining conformal engagement of surfaces at the lateral and medial interfaces while permitting increased tension of the medial collateral ligament at full extension, relaxed tension in both collateral ligaments during flexion, and stability of the joint at full flexion while permitting internal rotation of the lower leg.

While the above description constitutes the preferred embodiment of the present invention, it will be appreciated that the invention is susceptible to modification, variation and change without departing from the proper scope and fair meaning of the accompanying claims.

The invention claimed is:

1. A human knee prosthetic implant comprising:
   a tibia component forming a medial concave surface of the tibia component and a lateral concave surface of the tibia component, a projection extending from the tibia component and being disposed between the medial concave surface of the tibia component and the lateral concave surface of the tibia component, the projection forming a concave projection surface;
   a femur component forming a convex medial surface of the femur component and a lateral convex surface of the femur component, a central convex surface being disposed between the lateral convex surface of the femur component and the medial convex surface of the femur component;
   wherein the surfaces of the tibia and the femur component are formed such that in a state of full extension or partial flexion of the knee prosthetic implant, medial contact occurs between the medial concave surface of the tibia component and the convex medial surface of the femur component, and lateral contact occurs between the lateral concave surface of the tibia component and the lateral convex surface of the femur component and the central convex surface is disengaged from the concave projection surface, and wherein in a state of full flexion of the knee prosthetic implant, medial contact occurs between the medial concave surface of the tibia component and the convex medial surface of the femur component, and the lateral concave surface of the tibia component and the lateral convex surface of the femur component are separated, and the second convex surface is in contact with and engaged with the concave projection surface.

2. The human knee prosthetic implant in accordance with claim 1 wherein the central convex surface is formed by a central shaft extending between the lateral convex surface of the femur component and the medial convex surface of the femur component.

3. The human knee prosthetic implant in accordance with claim 2 further comprising the central shaft includes a medial element and a lateral element, the lateral element having a greater cross-sectional dimension than a diameter of the medial element.

4. The human knee prosthetic implant in accordance with claim 3 wherein the concave projection surface has a radius of curvature greater than a radius of curvature of the lateral element.

5. The human knee prosthetic implant in accordance with claim 3 further comprising the lateral element of the central shaft forming a cam profile outer surface engageable with the concave projection surface.

6. The human knee prosthetic implant in accordance with claim 1 further comprising the concave projection surface facing in a posterior direction.

7. The human knee prosthetic implant in accordance with claim 1 further comprising engagement between the second convex surface and the concave projection surface in the full flexion condition provides anterior-posterior stability for the knee prosthetic implant.

8. A human knee prosthetic implant comprising:
a tibia component forming first and second medial concave surfaces of the tibia component and a lateral concave surface of the tibia component, a projection extending from the tibia component and being disposed between the first and second medial concave surfaces of the tibia component and the lateral concave surface of the tibia component, the projection forming a concave projection surface;
a femur component forming first and second convex medial surfaces of the femur component and a lateral convex surface of the femur component, a central convex surface being disposed between the lateral convex surface of the femur component and the first and second medial convex surfaces of the femur component;
wherein the surfaces of the tibia and the femur components are formed such that in a state of full extension of the knee prosthetic implant medial contact occurs between the second medial concave surface of the tibia component and the second convex medial surface of the femur component, and lateral contact occurs between the lateral concave surface of the tibia component and the lateral convex surface of the femur component, and the central convex surface is disengaged from the concave projection surface, and wherein in a state of full flexion of the knee prosthetic implant, medial contact occurs between the first medial concave surface of the tibia component and the first convex medial surface of the femur component, and the lateral concave surface of the tibia component and the lateral convex surface of the femur component are separated, and the central convex surface is in contact with and engaged with the concave projection surface.

* * * * *